(12) United States Patent
Kawakami et al.

(10) Patent No.: US 8,067,446 B2
(45) Date of Patent: Nov. 29, 2011

(54) METHODS FOR TREATING AN ULCER OF THE SMALL INTESTINE AND STOMACH

(75) Inventors: Masakatsu Kawakami, Tokyo (JP); Yoshihiro Keto, Tokyo (JP); Ken Ikeda, Tokyo (JP); Mari Fukuda, Tokyo (JP); Junji Sato, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 12/280,668

(22) PCT Filed: Feb. 22, 2007

(86) PCT No.: PCT/JP2007/053310
§ 371 (c)(1),
(2), (4) Date: Aug. 25, 2008

(87) PCT Pub. No.: WO2007/097403
PCT Pub. Date: Aug. 30, 2007

(65) Prior Publication Data
US 2009/0036428 A1  Feb. 5, 2009

(30) Foreign Application Priority Data
Feb. 24, 2006 (JP) ................................. 2006-048914

(51) Int. Cl.
*A61K 31/381* (2006.01)
*A61K 31/415* (2006.01)
*A61K 31/425* (2006.01)
*A61K 31/4418* (2006.01)

(52) U.S. Cl. ......... 514/354; 514/365; 514/406; 514/448

(58) Field of Classification Search .......................... None
See application file for complete search history.

(56) References Cited

U.S. PATENT DOCUMENTS

| 5,614,520 | A | 3/1997 | Kondo et al. |
| 5,843,969 | A | 12/1998 | Ota et al. |
| 6,015,829 | A | 1/2000 | Ishibuchi et al. |
| 2007/0275950 | A1 | 11/2007 | Miyata et al. |
| 2008/0027048 | A1 | 1/2008 | Miyata et al. |

FOREIGN PATENT DOCUMENTS

| JP | 57 85379 | 5/1982 |
| JP | 59 95272 | 6/1984 |
| WO | 92 09279 | 6/1992 |
| WO | 96 31211 | 10/1996 |
| WO | 98 18765 | 5/1998 |
| WO | 2006 022374 | 3/2006 |
| WO | 2006 022375 | 3/2006 |

OTHER PUBLICATIONS

Karnam et al., Current Treatment Options in Gastroenterology, 4(1), (Feb. 1, 2001), pp. 15-21.*
Lazarotos et al., European Journal of Pharmacology, (Feb. 9, 2001), 413(1), pp. 121-129.*
Huh, Keun et al., "The Effect of Rebamipide on Gastric Xanthine Oxidase Activity and Type Conversion in Ethanol-Treated Rats", Free Radical Biology and Medicine, Elsevier, Science Inc., vol. 20, No. 7, pp. 967-971, (1996).
Dodo, Kenjiro et al., "Kyoketsu Saikanryu-Ammonia Fuka Rat no Kyusei Inenmaku Byohen (AGML) no Hassei ni Taisuru Troxipide no Yokusei Koka", Folia Pharmacologica Japonica, vol. 104, pp. 313-323, 1994, (with partial English translation).
Basivireddy, Jayasree et al., "Indomethacin-induced free radical-mediated changes in the intestinal brush border membranes", Biochemical Pharmacology, Elsevier, vol. 65, No. 4, pp. 683-695, (2003).
Khosravan, Reza et al., "Pharmacokinetic Interactions of Concomitant Administration of Febuxostat and NSAIDs", J Clin Pharmacol., vol. 46, No. 8, pp. 855-866, (2006).
Naito, Yuji et al., "Role of Oxygen Radical and Lipid Peroxidation in Indomethacin-Induced Gastric Mucosal Injury", Digestive Diseases and Sciences, vol. 43, No. 9, pp. 30S-34S (1998).
Zahavi, Ilan et al., "Oxygen Radical Scavengers are Protective Against Indomethacin-Induced Intestinal Ulceration in the Rat", Journal of Pediatric Gastroenterology Nutrition, vol. 21, No. 2, pp. 154-157, (1995).
Salim, Aws S. et al., "Role of Free Radical Scavengers in the Management of Refractory Duodenal Ulceration", Journal of Surgical Research, vol. 56, No. 1, pp. 45-52, (1994).
McAlindon, M E et al., "Effect of allopurinol, sulphasalazine, and vitamin C on aspirin induced gastroduodenal injury in human volunteers" Gut, vol. 38, pp. 518-524, (1996).
Moorhouse, P. Christopher et al., "Allopurinol and oxypurinol are hydroxyl radical scavengers", FEBS Letters 04481, vol. 213, No. 1, pp. 23-28, (1987).
Zhonghui Wen, et al., "Inflammatory Bowel Disease: Autoimmune or Immune-Mediated Pathogenesis", Clinical and Developmental Immunology, Sep./Dec. 2004, vol. 11, (3/4), pp. 194-204.
Seigo Ishibuchi, et al., "Synthesis and Structure—Activity Relationships of 1-Phenylpyrazoles as Xanthine Oxidase Inhibitors", Bioorganic & Medicinal Chemistry Letters 11 (2001) 879-882.
Koji Takeuchi, et al., "Roles of COX inhibition in pathogenesis of NSAID-induced small intestinal damage" Clinica Chimica Acta 411 (2010) 459-466.
S. J. Kontrurek, et al., "Prostaglandins and Ulcer Healing" Journal of Physiology and Pharmacology, 2005, 56, Supp 5, 5-31.
Arthur Kaser, et al., "Inflammatory Bowel Disease", Annu. Rev. Immunol. 2010.28:573-621.

(Continued)

*Primary Examiner* — Phyllis G. Spivack
(74) *Attorney, Agent, or Firm* — Oblon, Spivak, McClelland, Maier & Neustadt, L.L.P.

(57) ABSTRACT

A method for treating a digestive ulcer of the small intestine or stomach is disclosed with a non-purine xanthine oxidase inhibitor that is a carboxylic acid compound, wherein the non-purine xanthine oxidase inhibitor is a carboxylic acid compound of formula (I) or its salt and wherein the terms of formula (I) are herein defined:

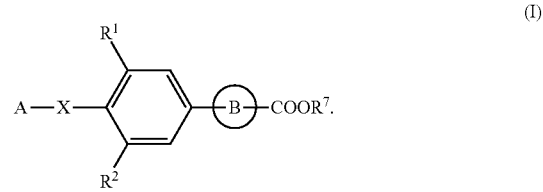

(I)

14 Claims, No Drawings

OTHER PUBLICATIONS

Y.H. Kho, et al., "Pharmacotherapeutic Options in Inflammatory Bowel Disease: An Update", Pharmacy World & Science, vol. 23, No. 1 (2001).

Jeffrey J. Ares, et al., "Gastroprotective Agents for the Prevention of NSAID-Induced Gastropathy", Current Pharmaceutical Design, vol. 4, No. 1, XP-002952634, Jan. 1, 1998, pp. 17-36.

Oa Al-Swayeh, et al., "Sucralfate attenuates gastric mucosal lesions and increased vascular permeability induced by ischaemia and reperfusion in rats", Journal of Gastroenterology and Hepatology, vol. 12, No. 7, XP-002586723, Jul. 1997, pp. 481-489.

Yuichiro J. Suzuki, et al., "Antioxidant Properties of Nitecapone (OR-462)", Free Radical Biology & Medicine, vol. 13, No. 5, XP-023523273, Nov. 1, 1992, pp. 517-525.

* cited by examiner

METHODS FOR TREATING AN ULCER OF THE SMALL INTESTINE AND STOMACH

CROSS-REFERENCE TO RELATED APPLICATIONS

This application is a 371 of PCT/JP2007/053310 filed Feb. 22, 2007 and claims the benefit of JP 2006-048914 filed Feb. 24, 2006.

TECHNICAL FIELD

The present invention relates to a pharmaceutical composition for treatment or prevention for digestive ulcer, comprising a non-purine-structure xanthine oxidase inhibitor as an active ingredient, in particular to a pharmaceutical composition for treatment or prevention for ulcer that are formed in digestive tracts by the attack thereto such as gastric acid, pepsin, stress, *Helicobacter pylori*, NSAID (non-steroidal antiinflammatory drug), etc.

BACKGROUND ART

The digestive ulcer indicates an ulcer in which the partial defect of the epithelial tissue in the mucosal layer of a digestive tract has reached the depth. The basic consideration for the reasons for the pathogenesis is a balance theory that the balance between the aggressive factor such as gastric acid, pepsin, stress, *Helicobacter pylori*, NSAID, etc. and the mucosal membrane protecting factors for digestive tracts, i.e., the equilibrium of the function of mucus/mucosa barrier and blood flow/microcirculation, growth factor and prostaglandin, may be lost to form an ulcer (*Chiryogaku*, 2005; 39(5): 8-10; Can. J. Gastroenterol., 1999, November; 13(9): 753-9). It has been considered that the main pathogenic sites of this disorder are upper digestive tracts such as stomach and duodenum; but with the recent technical development of capsule endoscopes, double balloon endoscopes, etc., it has been known that some ulcer may be formed even in small intestine which has heretofore been difficult to inspect (World J. Gastroenterol., 2005 Aug. 21; 11(31):4861-4). However, it has been reported that administration of the proton pump inhibitor, which is a standard medicine for a gastric/duodenal ulcer, is not effective for a small intestine ulcer (Gastroenterology, 2005 May; 128(5): 1172-8). From these, a pharmaceutical composition having a mechanism of widely effective for digestive ulcers not limited only to stomach/duodenum is desired.

Allopurinol is known as an agent for treating gout and hyperuricemia, and this compound inhibits xanthine oxidase to thereby exhibit the action of lowering the serum uric acid level (Am. J. Manag. Care., 2005 November; 11(15 Suppl.): S451-8). On the other hand, the compound has a nucleic acid-derived structure (purine-like structure), and many side effects have been reported, which are considered to be based on the inhibition of the nucleic acid metabolism (Am. J. Med. 1984 January; 76(1):47-56; Isr. Med. Assoc. J., 2005 October; 7(10): 656-60; Biol. Pharm. Bull., 1999 August; 22(8): 810-5). Therefore, recently, development of a non-nucleic acid structure xanthine oxidase inhibitor has been much studied; and for example, there are mentioned phenylazole-carboxylic acid derivatives such as 2-phenylthiazole derivatives (Patent References 1 to 3), 3-phenylisothiazole derivatives (Patent Reference 4 and Patent Reference 5), phenylpyrazole derivatives (Patent Reference 6, Patent Reference 7 and Patent Reference 8), 2-phenyloxazole derivatives (Patent Reference 9), 2-phenylimidazole derivatives (Patent Reference 9). There is no report showing the indication of these xanthine oxidase inhibitors for digestive ulcer.

Some reports say that allopurinol is effective for models with upper and lower digestive ulcers at an extremely high-level dose (Non-Patent References 1 to 3). Non-Patent Reference 1 has a description discussing that allopurinol has a xanthine oxidase-inhibiting effect and expresses the effect by inhibiting the production of free radicals. There is a clinical test report saying that a combination of allopurinol and cimetidine enhances the effect of curing duodenal ulcer (Non-Patent Reference 4). On the other hand, there is a report saying that allopurinol does not inhibit NSAID ulcer at a clinical dose to human (Non-Patent Reference 5). In addition, it is also reported that allopurinol has a purine-like structure, and its structure itself has a strong action of scavenging free radicals (Non-Patent Reference 6). As in the above, the effectiveness and the functional mechanism of allopurinol for animal models with digestive ulcer have been unclear.

Patent Reference 1: International Publication WO 92/09279
Patent Reference 2: JP-A 2002-105067
[Patent Reference 3: International Publication WO 96/31211
Patent Reference 4: JP-A 57-85379
Patent Reference 5: JP-A 6-211815
Patent Reference 6: JP-A 59-95272
Patent Reference 7: International Publication WO 98/18765
Patent Reference 8: JP-A 10-310578
Patent Reference 9: JP-A 6-65210
Non-Patent Reference 1: Biochemical Pharmacology, 2003, Vol. 65, pp. 683-695
Non-Patent Reference 2: Digestive Diseases and Sciences, 1998, Vol. 43, No. 9 (extra issue, 1998 September), pp. 30S-34S
Non-Patent Reference 3: Journal of Pediatric Gastroenterology and Nutrition, 1995, Vol. 21, pp. 154-157
Non-Patent Reference 4: Journal of Surgical Research, 1994, Vol. 56, No. 1, pp. 45-52
Non-Patent Reference 5: Gut, 1996, Vol. 38, pp. 518-524
Non-Patent Reference 6: FEBS LETTERS, 1987, Vol. 213, No. 1, pp. 23-28

DISCLOSURE OF THE INVENTION

Problems that the Invention is to Solve

An object of the present invention is to provide an agent for treating or preventing digestive ulcer, which is effective also for ulcer in small intestine on which gastric secretion inhibitors such as proton pump inhibitors exert no effect, and which is superior to allopurinol in efficaciousness and safety.

Means for Solving the Problems

The present inventors have made extensive studies and, as a result, found that a non-purine xanthine oxidase inhibitor shows a stronger antiulcer effect over allopurinol having a radical-scavenging effect based on a purine-like structure, and exhibits an excellent treating effect for gastric ulcer such as NSAID ulcer, and have completed the present invention. The above-mentioned Non-Patent References 1 to 3 describes that allopurinol is effective for a model with digestive ulcer but does not show the effectiveness for human (Non-Patent Reference 1), and animal models require a large amount of administration of 100 mg/kg. However, since allopurinol has a purine-like structure, its side effects have been reported (Am. J. Med., 1984 January; 76(1): 47-56; Isr. Med. Assoc. J., 2005 October; 7(10): 656-60; Biol. Pharm. Bull., 1999 August; 22(8): 810-5), and a high dose of 100 mg/kg effective for models with digestive ulcer cannot be employed in clinical practice. The above-mentioned Non-Patent Reference 4 describes that a combination of allopurinol and cimetidine enhanced the effect of treating human duodenal ulcer. On the other hand, the above-mentioned Patent Reference 5 describes that allopurinol did not inhibit NSAID-induced ulcer in human. Further, it has heretofore been known that allopurinol has a strong action of scavenging radicals based on the purine-like structure (Non-Patent Reference 6), but it is unclear on what the effect for suppressing digestive ulcer in animal is based. Accordingly, use of a compound having only a xanthine oxidase inhibiting effect for treatment of digestive ulcer has not been specifically noted. The present inventors have found that a group of compounds not having a purine-like structure but having a xanthine oxidase-inhibiting activity that differs from the type of allopurinol exhibit an excellent effect for treating gastric ulcer even though not having a radical scavenging effect based on the structure, and have completed the present invention.

The compounds described in Preparation Examples hereinunder are described in patent applications filed by the present patent applicant prior to the present patent application (PCT publications Nos. WO 2006/022374, WO 2006/022375 and PCT application PCT/JP2006/320061). These patent applications describe the applicability to autoimmune diseases such as inflammatory bowel disease, but has no disclosure relating to the applicability to digestive ulcer found in the present application.

Thus, the present invention relates to an agent for treating or preventing digestive ulcer, comprising a non-purine xanthine oxidase inhibitor as an active ingredient.

The present invention also relates to an agent for treating or preventing digestive ulcer, comprising a non-purine xanthine oxidase inhibitor as an active ingredient, wherein the inhibitor is a carboxylic acid derivative of the following general formula (I) or a salt thereof:

[Formula 1]

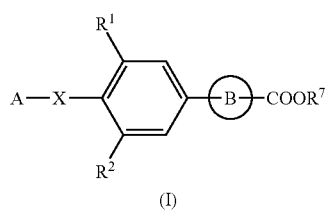

(I)

(wherein the symbols in the formula have the following meanings:
$R^1$: H or halogen,
$R^2$: —CN, —$NO_2$, halogeno-lower alkyl or —CO-lower alkyl,
A: linear or branched alkyl having from 1 to 8 carbon atoms, linear or branched alkenyl having from 2 to 8 carbon atoms, —Y-cycloalkyl, —Y-nitrogen-containing saturated heterocyclic group, —Y-oxygen-containing saturated heterocyclic group, —Y-optionally-condensed aryl, or —Y-heteroaryl;
wherein the linear or branched alkyl having from 1 to 8 carbon atoms and the linear or branched alkenyl having from 2 to 8 carbon atoms may be substituted with from 1 to 3, the same or different substituents selected from the following group G1; and the cycloalkyl, nitrogen-containing saturated heterocyclic group and the oxygen-containing saturated heterocyclic group may be substituted with from 1 to 4, the same or different groups selected from lower alkyl and the following group G1; and the optionally-condensed aryl and the heteroaryl may be substituted with from 1 to 3, the same or different groups selected from the following group G2;
G1 group: hydroxy, —CN, —O-lower alkyl, —S-lower alkyl, —$NR^3R^4$, —(CO)$NR^3(R^4)$, —$CO_2$—$R^5$ and halogen,
G2 group: halogen, —CN, —$NO_2$, lower alkyl, halogeno-lower alkyl, —O—$R^5$, —O-halogeno-lower alkyl, —O—CO—$R^5$, —O-benzyl, —O-phenyl, —$NR^3R^4$, —NH—CO—$R^5$, —$CO_2$—$R^5$, —CO—$R^5$, —CO—$NR^3R^4$, —CO-phenyl, —S—$R^5$, —$SO_2$-lower alkyl, —$SO_2$-phenyl, —NH—$SO_2$-naphthalene-$NR^3R^4$, phenyl, cycloalkyl and -lower alkylene-O—$R^5$;
$R^5$: H or lower alkyl;
$R^3$ and $R^4$: the same or different, each representing H or lower alkyl, and $R^3$ and $R^4$, taken together with the nitrogen atom to which they bond, may form a monocyclic nitrogen-containing saturated heterocyclic group;
Y: bond, lower alkylene, lower alkenylene, -(lower alkylene)-O— or -(lower alkylene)-O-(lower alkylene)-;
X: bond, —O—, —$N(R^6)$— or —S—;
$R^6$: H or lower alkyl,
ring B: monocyclic heteroaryl, wherein the monocyclic heteroaryl may be substituted with a group selected from lower alkyl, —OH and halogen; and
$R^7$: H or lower alkyl, and the same shall apply hereinunder).

The present invention further includes the following embodiments:
[1] Use of a non-purine xanthine oxidase inhibitor for the manufacture of an agent for treating or preventing digestive ulcer.
[2] A method of treating or preventing digestive ulcer, comprising administering an effective amount of a non-purine xanthine oxidase inhibitor to a patient.
[3] An agent for treating or preventing digestive ulcer, comprising a non-purine xanthine oxidase inhibitor as an active ingredient, which is administered to a patient under administration with a non-steroidal antiinflammatory drug.
[4] A combined preparation containing a non-purine xanthine oxidase inhibitor and a non-steroidal antiinflammatory drug.
[5] A combination for treating or preventing digestive ulcer, which is a combination of a preparation comprising a non-purine xanthine oxidase inhibitor as an active ingredient and a preparation comprising a non-steroidal antiinflammatory drug as an active ingredient, wherein the preparations are administered simultaneously or separately.

Effects of the Invention

The pharmaceutical composition of the present invention is useful as an agent for treating or preventing ulcer that formed in digestive tracts by the attack by gastric acid, pepsin, stress, *Helicobacter pylori*, NSAID, etc. The pharmaceutical composition of the present invention is more advantageous to conventional ulcer-treating agents such as proton pump inhibitors, in that it is effective even for ulcer in small intestine, for which gastric/duodenal ulcer-treating agents that inhibit gastric acid secretion such as proton pump inhibitors are ineffective.

BEST MODE FOR CARRYING OUT THE INVENTION

The present invention is described in detail hereinunder.
"Digestive ulcer" indicates an ulcer in which the partial defect of the epithelial tissue in the mucosal layer of a digestive tract has reached the depth. In particular, it means an ulcer formed in a digestive tract by the attack of gastric acid, pepsin, stress, *Helicobacter pylori*, NSAID, etc. "Digestive ulcer" quite differs from an ulcer formed in a digestive tract in autoimmune diseases such as inflammatory bowel disease. "Upper digestive ulcer" means the above-mentioned digestive ulcer that formed in esophagus, stomach and duodenum; and "lower digestive ulcer" means the above-mentioned digestive ulcer that formed in small intestine and large intestine. The agent for treating or preventing digestive ulcer of the present invention is an agent for treating or preventing the above-mentioned "digestive ulcer", and especially preferably, it is an agent for treating digestive ulcer in small intestine for which the treating effect of conventional gastric secretion inhibitors cannot be expected.

"Non-purine" means that the compound has no purine skeleton in the molecule. In this description, the purine skeleton means a ring skeleton of a bicyclic unsaturated hydrocarbon ring formed through condensation of a 5-membered ring and a 6-membered ring, which contains four nitrogen atoms. The purine skeleton includes "purine", which is the basic structure of purine nucleoside, or that is, "a ring skeleton formed through condensation of a pyridine ring and an imidazole ring", and in addition, analogues that differ in the position of the nitrogen atom, for example, pyrazolopyrimidine, etc. Accordingly, "non-purine xanthine oxidase inhibitor" is a xanthine oxidase inhibitor not having the above-mentioned purine skeleton in the molecule, and means other xanthine oxidase inhibitors than purine skeleton-having xanthine oxidase inhibitors (purine-type xanthine oxidase inhibitors) such as allopurinol or oxypurinol. The non-purine xanthine oxidase inhibitor does not have a purine-like structure, and therefore differs from the purine-type xanthine oxidase inhibitor in the manner of the enzyme inhibition and, in addition, has a common characteristic in that the structure-derived side effect is weak. The non-purine xanthine oxidase inhibitor includes, for example, the compounds of the above formula (I), the compounds described in the above-mentioned Patent References 1 to 9, and benzoxazole derivatives (WO 03/042185), triazole derivatives (WO 03/064410) and tetrazole derivatives (WO 2004/009563), but not limited thereto, and the inhibitor may be any others not having a purine skeleton and substantially not having an action of inhibiting purine biosynthesis.

In case where the agent for treating or preventing digestive ulcer of the present invention is used as combined preparations or drug combinations with NSAID for reducing the side effect of NSAID (non-steroidal antiinflammatory drug), the NSAID includes salicylic acid compounds (aspirin, salicylic acid), anthranilic acid compounds (mefenamic acid), phenylacetic acid compounds (dichlofenac, fenbufen), indole-acetic acid compounds (indomethacin, sulindac), isoxazole-acetic acid compounds (mofezolac), pyrano-acetic acid compounds (etodolac), naphthalene compounds (nabumetone), propionylacetic acid compounds (ibuprofen, ketoprofen, loxoprofen, naproxen, zaltoprofen), oxicam compounds (piroxicam, meloxicam, lornoxicam), and basic antiinflammatory drugs (tiaramide hydrochloride, emorfazone), etc. In addition, also mentioned are NSAIDs described in *Konnichi-nochiryoyaku*, 2005, pp. 86-115 (Nanko-do); Drugs 49(1): 51-70, 1995; and Drugs 52 (Suppl. 5): 13-23, 1996. However, NSAID is not limited to these, and can include any others that may induce ulceration by their administration.

In the definition of the general formulae in this description, the term "lower" means a linear or branched carbon chain having from 1 to 6 carbon atoms (hereinafter this may be abbreviated as "$C_{1-6}$"), unless otherwise specifically indicated. Accordingly, "lower alkyl" is $C_{1-6}$ alkyl, preferably linear alkyl such as methyl, ethyl, n-propyl, n-butyl, and branched alkyl such as isopropyl, isobutyl, tert-butyl, neopentyl. More preferred is $C_{1-4}$ alkyl; and even more preferred are methyl, ethyl, n-propyl, isopropyl and tert-butyl. "Lower alkylene" is $C_{1-6}$ alkylene, preferably linear alkylene such as methylene, ethylene, trimethylene, tetramethylene, and branched alkylene such as propylene, ethylethylene, 1,2-dimethylethylene, 1,1,2,2-tetramethylethylene. More preferred is $C_{1-4}$ alkylene.

The linear or branched alkyl having from 1 to 8 carbon atoms as A is preferably ethyl, n-propyl, isopropyl, n-butyl, isobutyl, isopentyl, neopentyl.

"Alkenyl" is a group having at least one double bond at any position of "alkyl", preferably $C_{2-8}$ alkenyl, more preferably $C_{2-8}$ alkenyl having at most 3 branches, even more preferably $C_{3-6}$ alkenyl having one double bond.

"Lower alkenylene" is a group having at least one double bond at any position of $C_{2-6}$ alkylene, preferably propenylene, butenylene, pentenylene, hexenylene, 1,3-butadienylene, more preferably $C_{3-4}$ alkenylene.

The linear or branched alkenyl having from 2 to 8 carbon atoms for A is preferably propenyl, butenyl, pentenyl, hexenyl, 1,3-butadienyl, isoprenyl, 3,3-dimethylpropen-2-yl.

"Halogen" indicates F, Cl, Br and I. Preferably, it is F and Cl. "Halogeno-lower alkyl" means $C_{1-6}$ alkyl substituted with at least one halogen, and is preferably $C_{1-6}$ alkyl substituted with at least one F, more preferably trifluoromethyl.

"Cycloalkyl" is a $C_{3-10}$ saturated hydrocarbon ring group, and may be bridged. Preferred is $C_{3-8}$ cycloalkyl; more preferred are cyclopropyl, cyclobutyl, cyclopentyl, cyclohexyl, cycloheptyl, cyclooctyl and adamantyl; and even more preferred are cyclopentyl, cyclohexyl and cycloheptyl.

"Aryl" is a $C_{6-14}$ monocyclic to tricyclic aromatic hydrocarbon ring group, and is preferably phenyl and naphthyl, more preferably phenyl. "Optionally condensed aryl" is a generic term for the above-mentioned "aryl" and, in addition, for phenyl condensed with a 5- to 7-membered saturated monocyclic hetero ring containing 1 or 2 O atoms, and phenyl condensed with a $C_{3-8}$ saturated hydrocarbon ring. "Optionally-condensed aryl" is preferably phenyl condensed with at least one ring selected from tetrahydrofuran, 1,3-dioxolane, 1,4-dioxepine, cyclohexane and cyclopentane, or non-condensed phenyl, and is more preferably non-condensed phenyl.

"Heteroaryl" is a generic term for a 5- or 6-membered monocyclic aromatic ring group having from 1 to 3 hetero atoms selected from O, S and N (monocyclic heteroaryl), and bicyclic or tricyclic heteroaryl constructed through condensation of the monocyclic heteroaryl rings or condensation of benzene ring and monocyclic heteroaryl ring. The monocyclic heteroaryl is preferably pyridyl, pyrrolyl, pyrazinyl, pyrimidinyl, pyridazinyl, imidazolyl, triazolyl, thienyl, furyl, thiazolyl, pyrazolyl, isothiazolyl, oxazolyl and isoxazolyl, more preferably thienyl, furyl, pyridyl, pyrrol-3-yl and pyrazol-4-yl. The bicyclic hetero aryl is preferably benzothienyl, benzofuryl, indazolyl, benzothiazolyl, benzoxazolyl, indolyl, benzimidazolyl, quinazolyl, quinoxalinyl, quinolyl, isoquinolyl, cinnolinyl and phthalazinyl, more preferably benzothienyl, benzofuryl, indazolyl and indolyl. The tricyclic heteroaryl is preferably carbazolyl, dibenzo[b,d]furanyl and dibenzo[b,d]thienyl.

In the above-mentioned "heteroaryl", the ring atom S may be oxidized to form an oxide or dioxide, or N may be oxidized to form an oxide.

The monocyclic heteroaryl of the ring B is preferably pyridyl, pyrrolyl, pyrazinyl, pyrimidinyl, pyridazinyl, imidazolyl, triazolyl, thienyl, furyl, thiazolyl, pyrazolyl, isothiazolyl, oxazolyl and isoxazolyl, more preferably pyridyl, thienyl, thiazolyl, pyrazolyl, isothiazolyl and isoxazolyl. The above-mentioned "monocyclic heteroaryl of the ring B" is described as a nomenclature of a monovalent group for the convenience' sake, but the cyclic group is a divalent group that bonds to benzene ring and carboxyl group.

"Oxygen-containing saturated heterocyclic group" is a 5- to 7-membered saturated monocyclic heterocyclic group containing one or two O atoms, and is preferably oxiranyl, oxetanyl, tetrahydrofuranyl and tetrahydropyranyl.

"Nitrogen-containing saturated heterocyclic group" is a 5- to 8-membered saturated or partially-unsaturated monocyclic heterocyclic group containing one N atom and optionally further containing one hetero atom of N, S and O (monocyclic nitrogen-containing saturated heterocyclic group), or a cyclic group constructed through condensation of the monocyclic nitrogen-containing saturated heterocyclic group with benzene ring. Preferred are pyrrolidinyl, piperidinyl, piperazinyl, azepanyl, diazepanyl, azocanyl, morpholinyl, thiomorpholinyl, tetrahydropyridyl, indolinyl, isoindolinyl, tetrahydroquinolyl, tetrahydroisoquinolyl and dihydrobenzoxazinyl. More preferred are pyrrolidinyl, piperidinyl, azepanyl, azocanyl and morpholinyl.

In the above-mentioned "nitrogen-containing saturated heterocyclic group", the ring atom S may be oxidized to form an oxide or dioxide, or N may be oxidized to form an oxide. In this, in addition, a carbon atom may be substituted with an oxo group.

Preferred embodiments of the compounds of formula (I) as an active ingredient of the pharmaceutical composition of the present invention are described below.

1) The compound where the benzene ring and —COOR$^7$ bonding to the ring B bonds to the ring B at any other positions than the adjacent positions.

2) The compound where the relative arrangement of the benzene ring and —COOR$^7$ bonding to the ring B is 1,3-positions.

3) More preferably, the compound of above 2) where the ring B is a divalent group of the following formula:

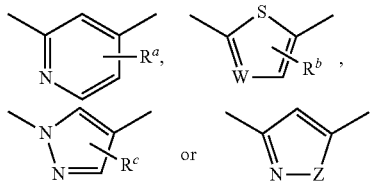

[Formula 2]

(wherein the symbols have the following meanings:
W: CH or N,
Z: O, S or NR$^d$,
R$^a$ to R$^c$: H, lower alkyl, or halogen, and
R$^d$: H or lower alkyl, the same shall apply hereinunder).

4) More preferably, the compound of above 3) wherein B is a cyclic group selected from pyridine, thiophene, thiazole and pyrazole rings.

5) More preferably, the compound of above 4) wherein X is —O— and A is linear or branched alkyl having from 1 to 8 carbon atoms and optionally substituted with a group of G1; the compound of above 4) where X is a bond and A is a monocyclic nitrogen-containing saturated heterocyclic group optionally substituted with a group of G1; or the compound of above 4) where X is a bond and A is aryl or heteroaryl optionally substituted with a group of G2.

6) More preferably, the compound of above 4) where X is —O— and A is lower alkyl; the compound of above 4) where X is a bond and A is a monocyclic nitrogen-containing saturated heterocyclic group; or the compound of above 4) where X is a bond and A is phenyl optionally substituted with a group of G2.

7) As another preferred embodiment, the compound of above 4) where R$^1$ is H, R$^2$ is CN, R$^7$ is H, R$^a$ to R$^c$ are H or methyl, X is —O— or a bond, A is "—O-lower alkyl" substituted phenyl, phenyl, or lower alkyl.

8) More preferably, a compound selected from 2-(2-cyanobiphenyl-4-yl)isonicotinic acid, 5-(2-cyanobiphenyl-4-yl)thiophene-2-carboxylic acid, 2-(2-cyanobiphenyl-4-yl)-4-methyl-1,3-thiazole-5-carboxylic acid, 2-(2-cyano-4'-methoxybiphenyl-4-yl)-4-methyl-1,3-thiazole-5-carboxylic acid, 1-(2-cyanobiphenyl-4-yl)-1H-pyrazole-4-carboxylic acid, 1-(2-cyano-4'-methoxybiphenyl-4-yl)-1H-pyrazole-4-carboxylic acid, 2-(2-cyanobiphenyl-4-yl)-1,3-thiazole-5-carboxylic acid, 2-(3-cyano-4-isobutyloxyphenyl)-4-methyl-1,3-thiazole-5-carboxylic acid, and 1-(3-cyano-4-neopentyloxyphenyl)-1H-pyrazole-4-carboxylic acid.

The monocyclic nitrogen-containing saturated heterocyclic group is preferably pyrrolidinyl, piperidinyl, azepanyl, azocanyl or morpholinyl. Preferred groups of G2 are halogen, —CN, lower alkyl, halogeno-lower alkyl, —O—R$^5$, —O-halogeno-lower alkyl, —S—R$^5$, —NR$^3$R$^4$, —CO$_2$—R$^5$ and -lower alkylene-O—R$^5$. The substituents for R$^a$ to R$^c$ are preferably H and methyl.

X is preferably a bond or —O—. A is preferably lower alkyl, monocyclic nitrogen-containing saturated heterocyclic group and phenyl. R$^2$ is preferably —CN and —NO$_2$, more preferably —CN. R$^7$ is preferably H.

The compounds as the active ingredient of the pharmaceutical composition of the present invention may include tautomers and optical isomers depending on the type of the substituent therein; and the present invention includes mixtures of those isomers or isolated isomers.

The compounds as the active ingredient of the pharmaceutical composition of the present invention include "pharmaceutically-acceptable prodrugs". "Pharmaceutically-acceptable prodrugs" are compounds that are metabolized in living bodies to give compounds having a group of CO$_2$H, NH$_2$, OH or the like for the active ingredient of the pharmaceutical composition of the present invention. The group of forming prodrugs includes those described in Prog. Med. 5:2157-2161 (1985); and those described in "Development of Medicines", Vol. 7, Molecular Design, pp. 163-198, Hirokawa Publishing, 1990.

Salts of the compounds as the active ingredient of the pharmaceutical composition of the present invention are pharmaceutically-acceptable salts, concretely including acid-addition salts with a mineral acid such as hydrochloric acid, hydrobromic acid, hydroiodic acid, sulfuric acid, nitric acid, phosphoric acid, or an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid. Depending on the type of the substituent therein, the compounds may form salts with a base, including, for example, salts with an inorganic base containing a metal such as sodium, potassium, magnesium, calcium, aluminium, lithium, or an organic base such as methylamine, ethylamine, ethanolamine, lysine, ornithine, and ammonium salts.

Further, the compounds or their salts as the active ingredient of the pharmaceutical composition of the present invention include various hydrates, solvates and polymorphic crystal substances.

(Production Method)

Typical production methods for the compounds as the active ingredient of the pharmaceutical composition of the present invention are described below. Of known non-purine xanthine oxidase inhibitors, those shown in the above-mentioned Patent References 1 to 9 may be produced with reference to the production methods described in those patent publications. Benzotriazole derivatives (WO 03/042185), triazole derivatives (WO 03/064410) and tetrazole derivatives (WO 2004/009563) may be produced with reference to the production methods described in the corresponding patent publications.

On the other hand, the compounds of formula (I) that are used as the active ingredient of the pharmaceutical composition of the present invention may be produced according to various known production methods, taking advantage of the characteristics based on the basic skeleton or the type of the substituent therein. In this case, depending on the type of the functional group therein, it may be often effective for the production technique to protect the functional group with a suitable protective group in a stage of starting compound or intermediate, or to substitute it with a group readily convertible into the functional group. The functional group includes, for example, an amino group, a hydroxyl group and a carboxyl group, and their protective groups are, for example, protective groups described in Protective Groups in Organic Synthesis (by T. W. Greene and P. G. M. Wuts), 3rd Ed., 1999. These may be used, as suitably selected in accordance with the reaction condition. The method comprises introducing the protective group, then reacting the compound, and if desired, removing the protective group or converting it into a desired group, thereby obtaining a desired compound.

The prodrugs of the compounds of formula (I) or their salts may be produced by introducing a specific group into the starting compound or intermediate, like the above-mentioned protective group, or by directly processing the compounds of formula (I). The reaction may be any ordinary esterification, amidation, acylation or the like known to those skilled in the art.

First Production Method:

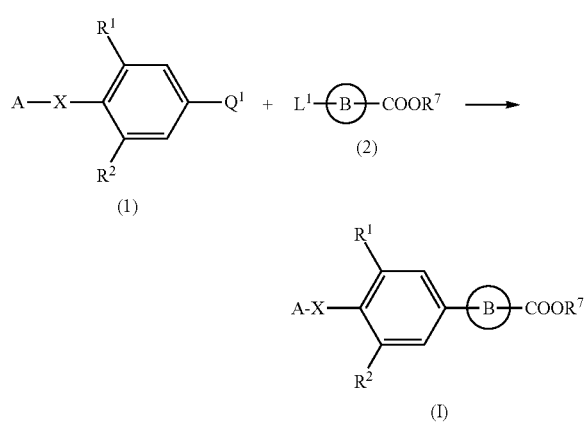

[Formula 3]

(In the formula, $Q^1$ represents —$B(OH)_2$ or —$B(OR^{11})OR^{12}$; $L^1$ represents a leaving group. In this, $R^{11}$ and $R^{12}$ are the same or different, each representing lower alkyl, or $R^{11}$ and $R^{12}$, taken together, form lower alkylene. The same shall apply hereinunder.)

This production method is for producing the compounds (I) of the present invention through coupling reaction of the compound (1) and the compound (2).

The leaving group for $L^1$ includes halogen, methanesulfonyloxy, p-toluenesulfonyloxy, trifluoromethanesulfonyloxy. In this production method, the compounds (1) and (2) are used in the same amount or any one of them is used excessively, and they are reacted in a solvent inert to the reaction in the presence of a base and a palladium catalyst at room temperature or under heat with reflux generally for 0.1 hours to 5 days. Preferably, the reaction is attained in an inert gas atmosphere. As the case may be, microwave radiation may be favorable for the heating in the reaction. Not specifically defined, the solvent includes, for example, aromatic hydrocarbons such as benzene, toluene, xylene; ethers such as diethyl ether, tetrahydrofuran (THF), 1,4-dioxane, 1,2-dimethoxyethane, 1,2-diethoxyethane; halogenohydrocarbons such as dichloromethane, 1,2-dichloroethane, chloroform; alcohols such as methanol, ethanol, 2-propanol, butanol; N,N-dimethylformamide (DMF), N-methylpyrrolidone (NMP), dimethylsulfoxide (DMSO), water; and their mixed solvents. The base is preferably an inorganic base such as sodium carbonate, potassium carbonate, sodium hydroxide, potassium hydroxide, sodium ethoxide, sodium methoxide. Also usable are other bases such as potassium fluoride, cesium fluoride. In this case, the reaction is preferably attained in an aprotic solvent. The palladium catalyst is preferably tetrakis(triphenylphosphine)palladium, dichlorobis(triphenylphosphine)palladium, palladium chloride-1,1'-bis(diphenylphosphino)ferrocene.

Second Production Method:

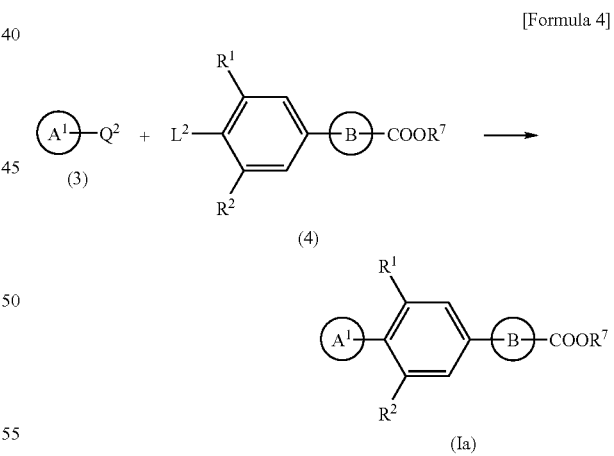

[Formula 4]

(In the formula, $A^1$ represents aryl or heteroaryl of the groups of A in formula (I); $Q^2$ is the same as $Q^1$; and $L^2$ is the same as $L^1$. The same shall apply hereinunder.)

This production method is a method for producing the compound (Ia) of the present invention where A is aryl or heteroaryl in formula (I), through coupling reaction of the compound (3) and the compound (4). The reaction reagents and the reaction conditions for the first production method are applicable also to this production method.

Third Production Method:

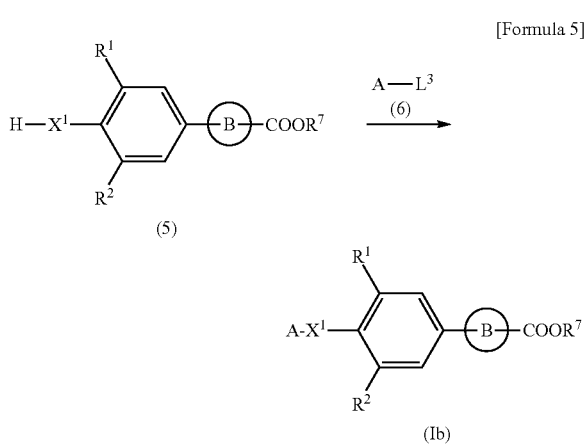

(In the formula, $X^1$ represents —O—, —N($R^6$)— or —S—; $L^3$ represents a leaving group or OH. The same shall apply hereinunder.)

This production method is a method for producing the compound (Ib) of the present invention where X is —O—, —N($R^6$)— or —S— in formula (I), through alkylation of the compound of formula (5).

The leaving group for $L^3$ includes halogen, methanesulfonyloxy, p-toluenesulfonyloxy, trifluoromethanesulfonyloxy.

In case where $L^3$ is a leaving group, this production method is as follows: The compound (5) and the alkylating agent (6) are used in the same amount of the alkylating agent (6) is used excessively, and they are reacted in a solvent inert to the reaction at room temperature or under heat with reflux generally for 0.1 hours to 5 days. Not specifically defined, the solvent includes aromatic hydrocarbons, ethers, halogenohydrocarbons, DMF, NMP, DMSO, and their mixed solvents, such as those mentioned hereinabove. As the case may be, the reaction is preferably attained in the presence of a base or a phase transfer catalyst. In this case, the base includes organic bases such as triethylamine, diisopropylethylamine (DIPEA), 1,8-diazabicyclo[5.4.0]-7-undecene (DBU); and inorganic bases such as sodium carbonate, potassium carbonate, cesium carbonate, sodium hydride. The phase transfer catalyst includes tetra-n-butylammonium chloride, tetra-n-butylammonium bromide, 18-crown-6.

In case where $L^3$ is OH and $X^1$ is O, the alkylation may be attained by using the compound (5) and the alkylating agent (6) in the same amount or by using the alkylating agent (6) excessively, and by processing them with an azodicarboxylic acid derivative such as ethyl azodicarboxylate or 1,1'-(azodicarbonyl)dipiperidine, and a phosphorus compound such as triphenyl phosphine or tributyl phosphine. Concrete reaction conditions and reaction reagents are described in detail in "Organic Reactions 42, 335-656, (1992); and "Journal of the Synthetic Organic Chemistry, Japan", 53, 631-641 (1997); and the alkylation may be attained according to the described methods or according to methods similar thereto.

Fourth Production Method:

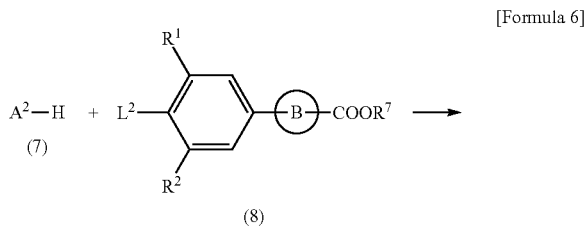

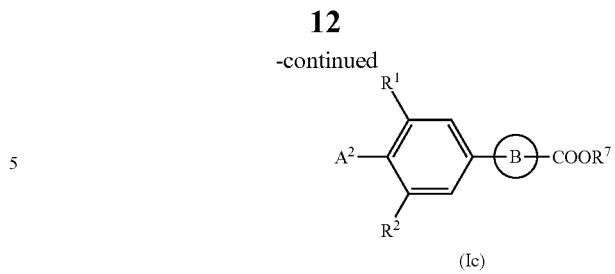

(In the formula, $A^2$ represents a nitrogen-containing heterocyclic group or heteroaryl containing at least one nitrogen atoms of the groups of A in formula (I), and this is a cyclic group bonding to the benzene ring via the nitrogen atom. The same shall apply hereinunder.)

This production method is a method for producing the compound (Ic) of the present invention through ipso-substitution between the compound (7) and the compound (8). The same condition for the alkylation of the above-mentioned third production method where $L^1$ is a leaving group, is applicable to this production method.

When A-N($R^6$)H (A and $R^6$ have the same meanings as above) is used in place of the compound of formula (7) in the same reaction as above, then a compound of formula (I) where X is —N($R^6$)— may be produced.

In the reaction of the above-mentioned first to fourth production methods, where a compound having a group of $CO_2H$ is used, it is desirable that the group is previously protected with a protective group and, after the intended reaction, the protective group is removed. Regarding the condition for the selection, protection and removal of the protective group, referred to are the method described in the above-mentioned Protective Groups in Organic Synthesis, 3rd Ed., 1999.

Other Production Methods:

The compounds of the present invention having various functional groups may also be produced according to methods obvious to those skilled in the art, or according to known production methods, or according to modifications of such methods. For example, the compounds of the present invention produced in the above-mentioned production methods may be further subjected to substituent modification reaction, thereby producing desired compounds of the present invention. Typical reactions are mentioned below.

(1) Amidation and Esterification:

Of the compounds (I) of the present invention, those having an amide group or those having an ester group may be produced, starting from a compound having a hydroxyl group or an amino group and reacting it with a carboxylic acid or its reactive derivative. For the reaction, for example, referred to are the methods described in "Courses in Experimental Chemistry", 4th Ed., Vol. 22 (1992), edited by the Chemical Society of Japan, Maruzen.

(2) Oxidation:

Of the compounds (I) of the present invention, those having a sulfonyl group or a sulfenyl group may be produced through oxidation of a compound having a sulfide group. For example, it may be attained according to the methods described in "Courses in Experimental Chemistry", 4th Ed., Vol. 23 (1991), edited by the Chemical Society of Japan, Maruzen.

(3) Alkylation:

Of the compounds (I) of the present invention, those having a lower alkoxy group or a lower alkylamino group may be produced through alkylation of a compound having a hydroxyl group or an amino group. The reaction may be attained under the same condition as in the third production method.

Production Methods for Starting Compounds:

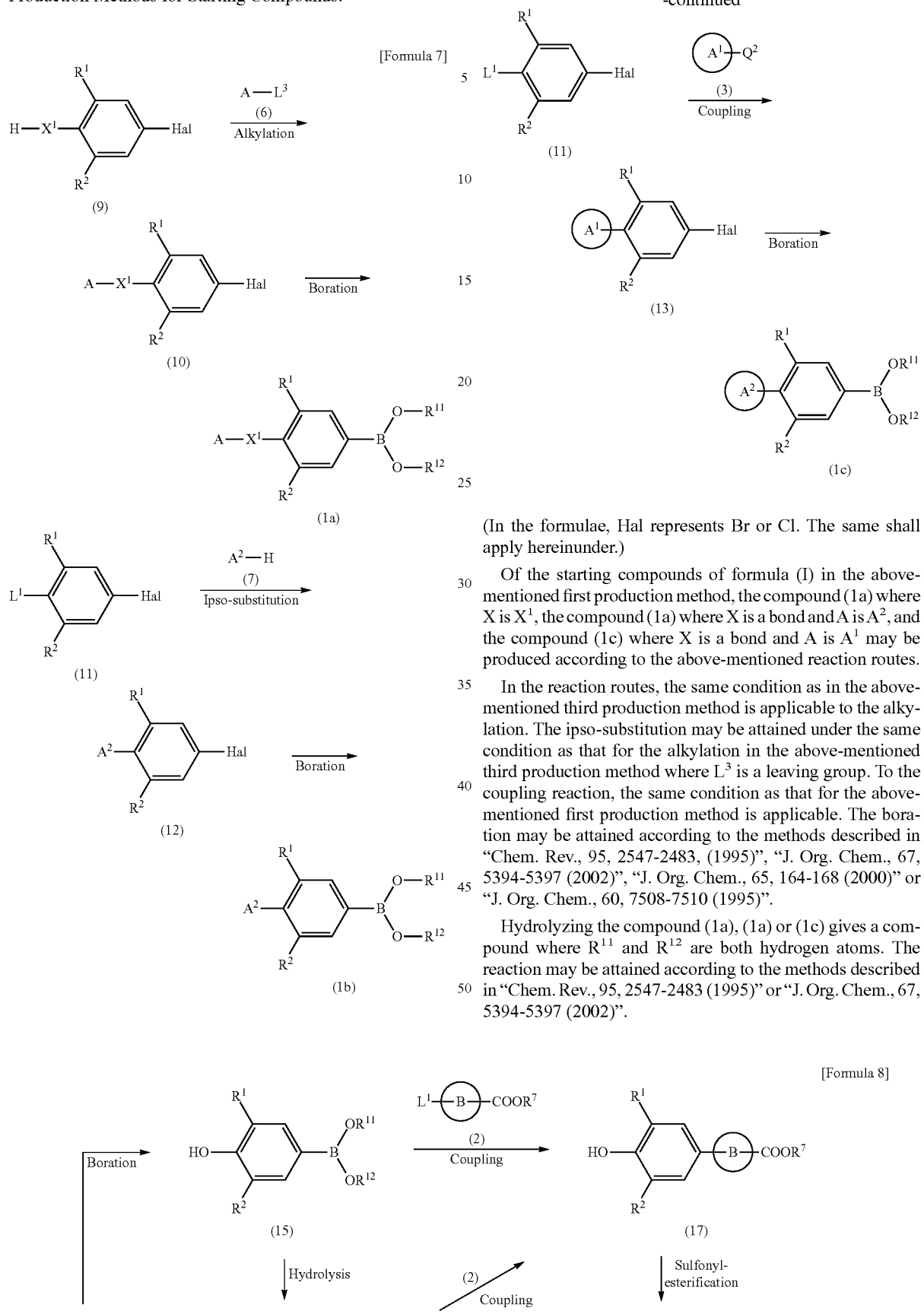

(In the formulae, Hal represents Br or Cl. The same shall apply hereinunder.)

Of the starting compounds of formula (I) in the above-mentioned first production method, the compound (1a) where X is $X^1$, the compound (1a) where X is a bond and A is $A^2$, and the compound (1c) where X is a bond and A is $A^1$ may be produced according to the above-mentioned reaction routes.

In the reaction routes, the same condition as in the above-mentioned third production method is applicable to the alkylation. The ipso-substitution may be attained under the same condition as that for the alkylation in the above-mentioned third production method where $L^3$ is a leaving group. To the coupling reaction, the same condition as that for the above-mentioned first production method is applicable. The boration may be attained according to the methods described in "Chem. Rev., 95, 2547-2483, (1995)", "J. Org. Chem., 67, 5394-5397 (2002)", "J. Org. Chem., 65, 164-168 (2000)" or "J. Org. Chem., 60, 7508-7510 (1995)".

Hydrolyzing the compound (1a), (1a) or (1c) gives a compound where $R^{11}$ and $R^{12}$ are both hydrogen atoms. The reaction may be attained according to the methods described in "Chem. Rev., 95, 2547-2483 (1995)" or "J. Org. Chem., 67, 5394-5397 (2002)".

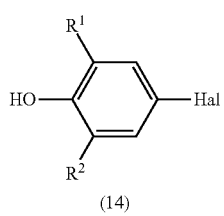

(14)

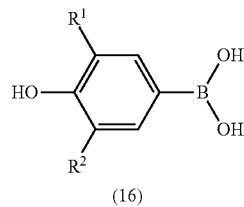

(16)

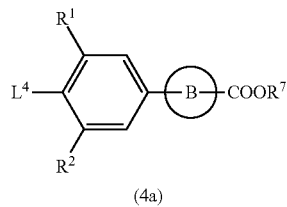

(4a)

(In the formula, $L^4$ represents sulfonyloxy such as methanesulfonyloxy, p-toluenesulfonyloxy or trifluoromethanesulfonyloxy.)

The starting compound (4a) can be produced according to the above-mentioned reaction route.

In the reaction route, the boration and the hydrolysis are the same as those in the above-mentioned production methods for starting compounds; and the coupling reaction may be attained under the same condition as in the above-mentioned first production method. The sulfonylesterification may be attained in an ordinary manner. In the reaction route, the phenolic hydroxyl group and the carboxyl group of the compounds are preferably protected with a protective group. Regarding the protective group and the condition for protection and deprotection, referred to are the methods described in the above-mentioned "Protective Groups in Organic Synthesis", 3rd Ed., 1999.

Using a compound derived from the compound (14) by substituting the hydroxyl group therein with halogen followed by reacting it similarly gives a compound corresponding to the compound (17) in which the hydroxyl group is substituted with halogen.

The compounds produced in the manner as above may be isolated and purified directly as they are free compounds or after salt formation in an ordinary manner as salts. The isolation and purification may be attained in ordinary chemical operation of extraction, concentration, distillation, crystallization, filtration, recrystallization or various chromatography.

Various isomers may be isolated in an ordinary manner, utilizing the difference in physicochemical properties between the isomers. For example, optical isomers may be separated and purified according to a method comprising introducing a racemic compound into a diastereomer salt with an optically-active organic acid (tartaric acid, etc.) followed by fractionation and crystallization, or a method of column chromatography using a chiral filler. Optically-active compounds may be produced, using suitable optically-active compounds as starting compounds. A diastereomer mixture may also be isolated through fractionating crystallization or chromatography.

The pharmaceutical composition of the present invention containing a non-purine xanthine oxidase inhibitor as the active ingredient may be formulated, using a carrier, a vehicle and other additives that are generally usable in ordinary pharmaceutical preparations.

The administration may be attained in any route of oral administration with tablets, pills, capsules, granules, powders or liquids, or parenteral administration with intravenous or injections for intramuscular injections, or suppositories, percutaneous preparations, nasal preparations or inhalants. The dose may be suitably determined for individuals, depending on the conditions, the age and the sex of the patients to which they are administered, but is, in general, from 0.001 to 100 mg/kg adult/day, more preferably from 0.01 to 30 mg/kg adult/day for oral administration, and this is administered all at a time or, as divided in portions, administered 2 to 4 times a day. In case of intravenous administration depending on the condition, in general, the dose may be from 0.0001 to 10 mg/kg adult/day, more preferably from 0.001 to 1 mg/kg adult/day, and this is administered all at a time or, as divided in portions, administered plural times a day. For inhalation, the dose may be from 0.0001 to 1 mg/kg adult/day, and this is administered all at a time or, as divided in portions, administered plural times a day. The content of the active ingredient in the preparation may be from 0.0001 to 80%, more preferably from 0.001 to 50%.

As the solid composition for oral administration of the present invention, employed are tablets, powders, granules, etc. The solid composition of those types comprises one or more active substances along with at least one inert diluent, such as lactose, mannitol, glucose, hydroxypropyl cellulose, microcrystalline cellulose, starch, polyvinyl pyrrolidone, magnesium meta-silicate aluminate. In an ordinary manner, the composition may contain any other additives, for example, a lubricant such as magnesium stearate, a disintegrator such as sodium carboxymethyl starch, and a dissolution promoter. If desired, the tablets and pills may be coated with sugar or with a gastric or enteric coating agent.

The liquid composition for oral administration includes pharmaceutically-acceptable emulsions, solutions, suspensions, syrups, elixirs and the like, which contain ordinary inert solvents such as purified water or ethanol. In addition to the inert solvents, those compositions may further contain pharmaceutical aids such as solubilizers, wetting promoters, suspension promoters, and also sweeteners, flavorings, aromas, and preservatives.

The injection for parenteral administration includes germ-free, water-base or water-free solutions, suspensions and emulsions. The water-base solvents include, for example, distilled water for injection and physiological saline water. The water-free solvents include, for example, propylene glycol, polyethylene glycol, vegetable oils such as olive oil, alcohols such as ethyl alcohol, Polysolvate 80 (Japan Pharmacopeia name), etc. Those compositions may further contain additives such as isotonicating promoters, preservatives, wetting promoters, emulsifiers, dispersants, stabilizers, dissolution promoters. These are sterilized by filtering them through bacteria-trapping filters, or by adding microbicides thereto, or by exposing them to radiations. The germ-free, solid compositions thus produced may be dissolved or suspended in germ-free water or in germ-free solvents for injection, before using them.

Transmucosal preparations such as inhalants or nasal preparations may be solid, liquid or semisolid, and may be produced in any conventional known methods. For example, a vehicle such as lactose or starch, and further a pH-controlling agent, a preservative, a surfactant, a lubricant, a stabilizer and a tackifier may be suitably added thereto. For administration, usable are suitable device for inhalation of insufflation. For example, using a known device or spray such as device for metering administration inhalation, the compound may be administered, as a powder of itself alone or a formulated mixture, or as a solution or suspension combined with a pharmaceutically-acceptable carrier. The dry powder inhalator may be for single use or repeated multiple use, for which usable are dry powder or powder-containing capsules. Further, it may also be a pressure aerosol spray or the like that uses a suitable propellant, for example, a suitable vapor such as chlorofluoroalkane, hydrofluoroalkane or carbon dioxide.

In producing suppositories, a low-melting point wax, for example, a fatty acid glyceride mixture or cocoa butter is melted, an active ingredient is added thereto, and uniformly dispersed by stirring. Next, this is injected into a suitable mold, cooled and solidified therein. The liquid preparation includes solution, suspension, retention enemas and emulsion, as well as water or aqueous propylene glycol solution.

In case where the pharmaceutical composition of the present invention is a combination or a mixture of an agent for treating or preventing digestive ulcer and a non-steroidal antiinflammatory drug, the amount of each ingredient may be suitably determined as the clinical effective amount thereof in its administration as a single preparation depending on the condition of each patient.

The agent for treating or preventing digestive ulcer of the present invention may be suitably combined with any other therapeutically-effective gastric secretion inhibitor, for example, a proton pump inhibitor or an $H_2$ blocker. In case of such combination, the two may form a combined preparation for simultaneous administration, or may form different preparations for separate administration.

PREPARATION EXAMPLES

The following Preparation Examples are to concretely demonstrate the production methods for the compounds of formula (I) as the active ingredient of the pharmaceutical composition of the present invention.

The abbreviations in Reference Preparation Examples, Preparation Examples and Tables Shown Below are as Follows:
Ex: Preparation Example Number, REx: Reference Preparation Example Number,
Dat: Physicochemical data (F:FAB-MS $(M+H)^+$,
FN: FAB-MS $(M-H)^-$, ES:ESI-MS $(M+H)^+$, ESN:ESI-MS $(M-H)^-$,
EI: EI-MS $(M)^+$, AP:API-ES-MS $(M+H)^+$, APN:API-ES-MS $(M-H)^-$, [the compound with (Na) after its mass-spectrometric data means that its Na salt or Na adduct gave the data; and the compound with (G-2W) after its mass-spectrometric data means that its glycerin adduct didehydrate gave the data],
NMR: δ (ppm) of characteristic peaks in $^1H$ NMR in DMSO-$d_6$,
NMRC: δ (ppm) of characteristic peaks in $^1H$ NMR in CDCl$_3$),
Anal: Elementary analysis, Calc. calculated data, Found: found data, H: Retention time (min) in HPLC under the following condition, [HPLC condition: column, Wakosil-II 5C18AR 5 μm, 2.0×30 mm; detection wavelength, 254 nm; measuring temperature, 35.0° C.; solvent, started in aqueous 5 mM trifluoroacetic acid solution/MeOH=9/1, and the ratio was changed to 0/10 within 4 minutes, and afterwards, the sample was eluted at 0/10 for 0.5 minutes, the flow rate was 1.2 ml/min]), Str: Structural formula,
Syn: Production method (Numeral means the Preparation Example Number as referred to in producing the compound in the same manner),
Sal: Salt (the compound with no mark is a free base, the compound designated by 0.3HCl means that it is a mixture of monohydrochloride and free base in a molar ratio of 0.3/0.7),
Me: methyl; Et ethyl; nPr: n-propyl; iPr: isopropyl; cPr: cyclopropyl; nBu: n-butyl; iBu: isobutyl; tBu: tert-butyl; cBu: cyclobutyl; nPen: n-pentyl, iPen: isopentyl, cPen: cyclopentyl, nHex: n-hexyl, cHex: cyclohexyl, cHep: cycloheptyl, cOct: cyclooctyl, Bn: Benzyl, Ph: Phenyl, 2Py: 2-Pyridyl, 3Py: 3-Pyridyl, 4Py: 4-Pyridyl, 2Thie: 2-Thienyl, 3Thie: 3-Thienyl, 2Fur: 2-Furyl, 3Fur: 3-Furyl, 1Naph: 1-Naphthyl, 2Naph: 2-Naphthyl, Ac: Acetyl, and Tf: Trifluoromethanesulfonyl.

A substituted phenyl group is represented as "numeral indicating the substituent position-abbreviation of the substituent-Ph" in the Tables. "di" before the substituent means that the group has two substituents. For example, 4-MeO-3,5-diMe-Ph- means 4-methoxy-3,5-dimethylphenyl group.

In the column "Syn" relative to the production method in the Tables below, the same Preparation Example Number is given to the compounds of which the salt forms differ but which were produced through the same type of reaction. Interconversion between a free base and its salt is a technical common sense of those skilled in the art.

Reference Preparation Example 1

5-Bromo-2-hydroxybenzonitrile, isobutyl bromide, and potassium carbonate were heated at 80° C. in DMF in the presence of tetra-n-butylammonium bromide to obtain 5-bromo-2-isobutoxybenzonitrile. F: 254, 256.

Reference Preparation Example 2

After 2,2-dimethyl-1-propanol and sodium hydride were stirred at 0° C. in DMF, 5-bromo-2-fluorobenzonitrile was added thereto, followed by reaction at room temperature to obtain 5-bromo-2-(2,2-dimethylpropoxy)benzonitrile. NMRC: 3.67 (2H, s), 6.83 (1H, d), 7.64 (1H, d).

Reference Preparation Example 3

5-Bromo-2-fluorobenzonitrile and piperidine were heated at 80° C. in DMSO in the presence of cesium carbonate to obtain 5-bromo-2-piperidin-1-ylbenzonitrile. F: 265.

Reference Preparation Example 4

5-Bromo-2-isobutoxybenzonitrile and triisopropyl borate were dissolved in a mixed solvent of THF and toluene and an n-butyllithium-hexane solution was added dropwise to the solution at a temperature below −60° C. After the temperature was elevated to −20° C., 1M hydrochloric acid was added, followed by stirring at room temperature to obtain (3-cyano-4-isobutoxyphenyl)boronic acid. F: 220.

Reference Preparation Example 5

[4-(Benzyloxy)-3-cyanophenyl]boric acid and methyl 2-chloroisonicotinate were dissolved in a mixture liquid of toluene and an aqueous 2 M sodium carbonate solution, and in the presence of tetrakis(triphenylphosphine)palladium, the mixture was stirred under heating in an argon atmosphere at 100° C. to obtain methyl 2-[4-(benzyloxy)-3-cyanophenyl]isonicotinate. F: 345.

Reference Preparation Example 6

Methyl 2-[4(benzyloxy)-3-cyanophenyl]isonicotinate and pentamethylbenzene were heated under reflux temperature in trifluoroacetic acid to obtain methyl 2-(3-cyano-4-hydroxyphenyl)isonicotinate. F: 255.

Reference Preparation Example 7

Methyl 3-fluoroisonicotinate was oxidized with 3-chloroperbenzoic acid, followed by heating in the presence of phosphoryl chloride. The product was separated by silica gel column chromatography to obtain methyl 2-chloro-5-fluoroisonicotinate (EI: 189) and methyl 2-chloro-3-fluoroisonicotinate (EI: 189).

Reference Preparation Example 8

Methyl 2-(3-cyano-4-hydroxyphenyl)isonicotinate and N-chlorosuccinimide were stirred at room temperature in acetonitrile to obtain methyl 2-(3-chloro-5-cyano-4-hydroxyphenyl)isonicotinate. ES: 289.

Reference Preparation Example 9

Methyl 2-(3-cyano-4-hydroxyphenyl)isonicotinate and N-bromosuccinimide were stirred at room temperature in acetonitrile to obtain methyl 2-(3-bromo-5-cyano-4-hydroxyphenyl) isonicotinate. FN: 333.

Reference Preparation Example 10

Sodium hydride was added to a DMF solution of 2,3-difluorobenzonitrile and 2-(methylsulfonyl)ethanol, followed by stirring at room temperature to obtain 3-fluoro-2-hydroxybenzonitrile. FN: 136.
3-Fluoro-2-hydroxybenzonitrile and N-bromosuccinimide were stirred at room temperature in acetonitrile to obtain 5-bromo-3-fluoro-2-hydroxybenzonitrile. EI: 215, 217.

Reference Preparation Example 11

(3-Cyano-4-benzyloxy-5-fluorophenyl)boronic acid and methyl 2-chloroisonicotinate were dissolved in a mixed solution of toluene and a 2M aqueous sodium carbonate solution, followed by heating under reflux for 3 hours in the presence of tetrakis(triphenylphosphine)palladium to obtain methyl 2-(3-cyano-4-benzyloxy-5-fluorophenyl)isonicotinate. F: 363.
Methyl 2-(3-cyano-4-benzyloxy-5-fluorophenyl)isonicotinate is stirred at room temperature in methanol-THF (1:1) under a hydrogen atmosphere at normal pressure in the presence of palladium-carbon to obtain methyl 2-(3-cyano-5-fluoro-4-hydroxyphenyl)isonicotinate. FN: 271.

Reference Preparation Example 12

Cesium fluoride and tetrakis(triphenylphosphine)palladium were added to a 1,2-dimethoxyethane solution of (3-cyano-4-fluorophenyl)boronic acid and methyl 2-chloroisonicotinate, and the mixture was heated under reflux under an argon atmosphere to obtain methyl 2-(3-cyano-4-fluorophenyl)isonicotinate. F: 257.

Reference Preparation Example 13

(4-Benzyloxy-3-cyanophenyl)boronic acid and methyl 4,5-dibromo-3-fluorothiophene-2-carboxylate were dissolved in a mixed solution of toluene and a 1M aqueous sodium carbonate solution and the whole was heated at 110° C. for 2.5 days in the presence of tetrakis(triphenylphosphine)palladium to obtain methyl 4-bromo-5-(4-benzyloxy-3-cyanophenyl)-3-fluorothiophene-2-carboxylate. Methyl 4-bromo-5-(4-benzyloxy-3-cyanophenyl)-3-fluorothiophene-2-carboxylate and triethylamine were stirred at room temperature in 1,4-dioxane under a hydrogen atmosphere at normal pressure in the presence of palladium-carbon to obtain methyl 5-(3-cyano-4-hydroxyphenyl)-3-fluorothiophene-2-carboxylate. FN: 276.

Reference Preparation Example 14

A 4M HCl/1,4-dioxane solution was added to a DMF solution of 4-(benzyloxy)isophthalonitrile and thioacetamide, followed by stirring at 60° C. to obtain 4-(benzyloxy)-3-cyanobenzenecarbothioamide. AP: 291 (Na).

Reference Preparation Example 15

4-(Benzyloxy)-3-cyanobenzenecarbothioamide and ethyl 2-chloroacetacetate were stirred in ethanol at 75° C. to obtain ethyl 2-[4-(benzyloxy)-3-cyanophenyl]-4-methyl-1,3-thiazole-5-carboxylate. AP: 401(Na).

Reference Preparation Example 16

4-(Benzyloxy)-3-cyanobenzenecarbothioamide and methyl 2-chloro-3-oxopropionate were heated under reflux in 1-butanol in the presence of Molecular Sieves 4A to obtain methyl 2-[4-(benzyloxy)-3-cyanophenyl]-1,3-thiazole-5-carboxylate. AP: 373(Na).

Reference Preparation Example 17

Ethyl 2-[4-(benzyloxy)-3-cyanophenyl]-4-methyl-1,3-thiazole-5-carboxylate was suspended in a mixture of THF and ethanol, then palladium-carbon was added thereto, and the mixture was stirred under a hydrogen atmosphere at room temperature to obtain ethyl 2-(3-cyano-4-hydroxyphenyl)-4-methyl-1,3-thiazole-5-carboxylate. APN: 287.

Reference Preparation Example 18

Methyl 2-(3-cyano-4-hydroxyphenyl)isonicotinate and trifluoromethanesulfonic anhydride were reacted at 0° C. in dichloromethane in the presence of diisopropylethylamine to obtain methyl 2-(3-cyano-4-{[(trifluoromethyl)sulfonyl]oxy}phenyl)isonicotinate. F: 387.

Reference Preparation Example 19

5-Bromo-2-iodobenzonitrile and 3-pyridylboric acid were dissolved in a mixture solution of aqueous 2 M sodium carbonate solution and toluene, then tetrakis(triphenylphosphine)palladium was added thereto, and the mixture was heated, stirred with heating in an argon atmosphere at 100° C. for 3 days to obtain 5-bromo-2-pyridin-3-ylbenzonitrile. EI: 258, 260.

Reference Preparation Example 20

Methyl 2-(3-cyano-4-fluorophenyl)isonicotinate and sodium azide were dissolved in a DMF solution, followed by stirring at 50° C. for 4 hours to obtain methyl 2-(4-azido-3-cyanophenyl)isonicotinate. NMRC: 7.38 (1H, d), 7.84 (1H, dd), 8.46 (1H, d)

Reference Preparation Example 21

5-Formyl-2-methoxybenzonitrile, sodium acetate and hydroxyamine were dissolved in ethanol, followed by stirring at 80° C. for 6 hours to obtain 5-[(hydroxyimino)methyl]-2-methoxybenzonitrile. APN: 175.

Reference Preparation Example 22

5-[(Hydroxyimino)methyl]-2-methoxybenzonitrile, 4 M hydrochloric acid and Oxon (registered trade name) were dissolved in a DMF solution, followed by stirring at room temperature for 12 hours to obtain 3-cyano-N-hydroxy-4-methoxybenzenecaboximidoyl chloride. NMRC: 7.01 (1H, d), 8.03 (1H, dd), 8.07 (1H, d).

Reference Preparation Example 23

3-Cyano-N-hydroxy-4-methoxybenzenecaboximidoyl chloride, ethyl propiolate and triethylamine were dissolved in a THF solution, followed by stirring at 40° C. to obtain ethyl 3-(3-cyano-4-methoxyphenyl)-5-isoxazolecarboxylate. AP: 295.

Reference Preparation Example 24

Ethyl 3-(3-cyano-4-methoxyphenyl)-5-isoxazolecarboxylate and tribromoborane were dissolved in a dichloromethane solution, followed by stirring for 2 hours under ice-cooling. Further, the mixture was stirred at 40° C. for 30 minutes to obtain ethyl 3-(3-cyano-4-hydroxyphenyl)-5-isoxazolecarboxylate. APN: 257.

Reference Preparation Example 25

Palladium-carbon was added to a methanol solution of methyl 2-(4-azido-3-cyanophenyl)isonicotinate, and the mixture was stirred in the presence of hydrogen gas at room temperature for 5 hours to obtain methyl 2-(4-amino-3-cyanophenyl)isonicotinate. AP: 254.

Reference Preparation Example 26

Methyl 5-(4-hydroxyphenyl)thiophene-2-carboxylate was obtained in accordance with the method of Reference Preparation Example 6 using methyl 5-(4-benzyloxyphenyl)thiophene-2-carboxylate and pentamethylbenzene. F: 233.

Sodium hydride and acetic anhydride were added to a THF solution of methyl 5-(4-hydroxyphenyl)thiophene-2-carboxylate and the whole was stirred at room temperature to obtain methyl 5-[4-(acetyloxy)phenyl]thiophene-2-carboxylate. ES: 277.

Aluminum chloride was added to a chlorobenzene solution of methyl 5-[4-(acetyloxy)phenyl]thiophene-2-carboxylate and the whole was stirred at 120° C. to obtain methyl 5-(3-acetyl-4-hydroxyphenyl)thiophene-2-carboxylate. F: 277.

Reference Preparation Example 27-65

Starting from the corresponding starting compounds, compounds of Reference Preparation Examples 27 to 31 were produced in the same manner as in Reference Preparation Example 1, compounds of Reference Preparation Examples 32 to 36 were produced in the same manner as in Reference Preparation Example 2, a compound of Reference Preparation Example 37 was produced in the same manner as in Reference Preparation Example 3, compounds of Reference Preparation Examples 38 to 50 were produced in the same manner as in Reference Preparation Example 4, a compound of Reference Preparation Example 51 was produced in the same manner as in Reference Preparation Example 5, a compound of Reference Preparation Example 52 was produced in the same manner as in Reference Preparation Example 6, a compound of Reference Preparation Example 53 was produced in the same manner as in Reference Preparation Example 11, a compound of Reference Preparation Example 54 was produced in the same manner as in Reference Preparation Example 12, a compound of Reference Preparation Example 55 was produced in the same manner as in Reference Preparation Example 15, compounds of Reference Preparation Examples 56 to 57 were produced in the same manner as in Reference Preparation Example 17, compounds of Reference Preparation Examples 58 to 65 were produced in the same manner as in Reference Preparation Example 18. As the starting compound in Reference Preparation Examples 62 and 64, used was the phenol compound described in Patent References 7 and 8. The structures and the physicochemical data of the compounds of Reference Preparation Examples 27 to 65 are shown in Table 1 to 2 below.

Reference Preparation Example 66

20% sodium ethoxide and isoamyl nitrite were added to and dissolved in an ethanol solution of 5-(cyanomethyl)-2-methoxybenzonitrile. Isopropyl alcohol was added, and the precipitate formed was collected by filtration. The resulting solid and 4-methylbenzenesulfonyl chloride were dissolved in ethanol, and the solution was refluxed for 5 hours to obtain 5-[cyano({[(4-methylphenyl)sulfonyl]oxy}imino)methyl]-2-methoxybenzonitrile. AP: 378.

Reference Preparation Example 67

Ethyl sulfanylacetate and triethylamine were dissolved in an ethanol solution of 5-[cyano({[(4-methylphenyl)sulfonyl]oxy}imino)methyl]-2-methoxybenzonitrile, followed by stirring for 5 hours under ice-cooling to obtain ethyl 4-amino-3-(3-cyano-4-methoxyphenyl)isothiazole-5-carboxylate. AP: 378.

Reference Preparation Example 68

3-Methylbutyl nitrate was dissolved in a tetrahydrofuran solution of ethyl 4-amino-3-(3-cyano-4-methoxyphenyl)isothiazole-5-carboxylate, followed by heating under reflux for 5 hours to obtain ethyl 3-(3-cyano-4-methoxyphenyl)isothiazole-5-carboxylate. AP: 311.

Reference Preparation Example 69

Under ice-cooling, boron tribromide was added to a dichloromethane solution of ethyl 3-(3-cyano-4-methoxyphenyl)isothiazole-5-carboxylate, followed by stirring for 1 hour and then stirring at 40° C. for 3 hours to obtain ethyl 3-(3-cyano-4-hydroxyphenyl)isothiazole-5-carboxylate. AP: 297.

Preparation Example 1

(1) In a mixed solution of 50 ml of toluene and 30 ml of a 2M aqueous sodium carbonate solution were dissolved 1.46 g of (3-cyano-4-isobutoxyphenyl)boronic acid and 1.86 g of methyl 2-chloroisonicotinate, and the resulting solution was heated at 100° C. for 1 hour in the presence of 0.49 g of tetrakis(triphenylphosphine)palladium. The reaction solution was extracted with ethyl acetate and the organic layer was washed with brine and then dried and concentrated under reduced pressure. The residue was purified by silica gel column chromatography (hexane:ethyl acetate:chloroform=70:15:15) to obtain 1.98 g of methyl 2-(3-cyano-4-isobutoxyphenyl)isonicotinate.

(2) Then, 1.98 g of the compound was dissolved in a mixed solution of 30 ml of methanol and 70 ml of THF, and 9 ml of a 1M aqueous sodium hydroxide solution was added thereto, followed by heating at 50° C. for 1 hour.

After cooling, the resulting solution was neutralized with 1M hydrochloric acid and then extracted with chloroform, followed by washing with brine. After the solution was dried, concentration was performed under reduced pressure and the resulting residue was recrystallized from a mixed solvent of ethanol and water to obtain 1.66 g of 2-(3-cyano-4-isobutoxyphenyl)isonicotinic acid.

Preparation Example 2

(1) In 5 ml of DMF were dissolved 82 mg of methyl 2-(3-cyano-4-hydroxyphenyl)isonicotinate and 66 mg of isopropyl iodide, and the resulting solution was heated at 80° C. for 3 hours in the presence of 72 mg of potassium carbonate and 10 mg of tetra-n-butylammonium bromide. The reaction solution was cooled and then diluted with water, followed by extraction with ethyl acetate. The organic layer was washed with brine and then dried and concentrated under reduced pressure. The resulting residue was washed with a mixed solvent (hexane:ethyl acetate=10:1) to obtain 91 mg of methyl 2-(3-cyano-4-isopropoxyphenyl)isonicotinate.

(2) Then, 86 mg of the compound was dissolved in a mixed solution of 3 ml of methanol and 3 ml of THF, and 0.35 ml of a 1M aqueous sodium hydroxide solution was added thereto, followed by heating at 60° C. for 1 hour. After being cooled to room temperature, the resulting solution was diluted with diisopropyl ether and water and an aqueous layer was separated. The aqueous layer was neutralized with 1M hydrochloric acid and then extracted with ethyl acetate. After being washed with water, the organic layer was dried and concentrated under reduced pressure to obtain 55 mg of 2-(3-cyano-4-isopropoxyphenyl)isonicotinic acid.

Preparation Example 3

(1) In 5 ml of THF were dissolved 63 mg of 3-(methylthio)-1-propanol and 100 mg of methyl 2-(3-cyano-4-hydroxyphenyl)isonicotinate, and the resulting solution was heated at 0° C. for 10 minutes in the presence of 0.15 ml of tributylphosphine and 149 mg of 1,1'-(azodicarbonyl)dipiperidine. Then, the reaction solution was warmed to room temperature and stirred all day and night. After removal of the solvent, water was added and extraction with ethyl acetate was performed. The resulting organic layer is washed with brine and then dried and concentrated under reduced pressure. The resulting residue was purified by silica gel column chromatography (chloroform:methanol=95:5) to obtain 92 mg of methyl 2-{3-cyano-4-[3-(methylthio)propoxy]phenyl}isonicotinate.

(2) Then, 92 mg of the compound was dissolved in a mixed solution of 3 ml of methanol and 3 ml of THF, and 0.32 ml of a 1M aqueous sodium hydroxide solution was added thereto, followed by heating at 60° C. for 1 hour. After being cooled, the reaction solution was diluted with diisopropyl ether and an aqueous layer was separated. The aqueous layer was neutralized with 1M hydrochloric acid and then extracted with ethyl acetate. After washing with brine, the organic layer was dried and concentrated under reduced pressure to obtain 81 mg of 2-{3-cyano-4-[3-(methylthio)propoxy]phenyl} isonicotinic acid.

Preparation Example 4

(1) In 7 ml of DMSO was dissolved 2.22 g of methyl 2-(3-cyano-4-fluorophenyl)isonicotinate, and 2.44 ml of hexamethyleneimine was added thereto, followed by heating at 50° C. for 5 hours. After cooling, the reaction solution was diluted with ethyl acetate and was washed with 1M hydrochloric acid, a saturated aqueous sodium hydrogen carbonate solution, and brine, successively. The organic layer was dried and then concentrated under reduced pressure and the resulting residue was dissolved in a mixed solvent of ethyl acetate and diisopropyl ether. Activated carbon was added thereto, followed by stirring for 1 hour. Then, the activated carbon was removed by filtration and washed with ethyl acetate. The resulting filtrate and washing liquid were combined and concentrated to obtain 2.58 g of methyl 2-(4-azepan-1-yl-3-cyanophenyl)isonicotinate.

(2) Then, 2.49 g of the compound was dissolved in a mixed solvent of 15 ml of methanol and 30 ml of THF, and 11 ml of a 1M aqueous sodium hydroxide solution was added thereto, followed by heating at 80° C. for 1 hour.

After cooling, the reaction solution was concentrated under reduced pressure. Then, water was added, followed by washing with diisopropyl ether. The resulting aqueous layer was filtered and then neutralized with 1M hydrochloric acid. The precipitated crystals were collected by filtration and washed with water and ethanol, successively. The crude crystals were recrystallized from a mixed solvent of DMSO and water to obtain 2.07 g of a salt free compound of 2-(4-azepan-1-yl-3-cyanophenyl)-isonicotinate. 295 mg of the free compound obtained in a similar manner was suspended in a mixed solvent of 4 ml of ethanol and 2 ml of THF, and 0.46 ml of a 4M hydrogen chloride-ethyl acetate solution was added thereto. After stirring at room temperature for 30 minutes, the precipitated crystals were collected by filtration to obtain 279 mg of 2-(4-azepan-1-yl-3-cyanophenyl)isonicotinic acid monohydrochloride.

Preparation Example 5

(1) In 0.4 ml of 1,4-dioxane were dissolved 237 mg of methyl 2-(3-cyano-4-{[(trifluoromethyl)sulfonyl]oxy}-phenyl) isonicotinate and 0.4 ml of heptamethyleneimine, followed by heating at 90° C. for 1 hour. After the reaction solution was cooled, purification by silica gel column chromatography (hexane:ethyl acetate:chloroform=80:10:10) was performed to obtain 23 mg of 2-(4-azocan-1-yl-3-cyanophenyl)isonicotinate.

(2) Then, 22 mg of the compound was dissolved in a mixed solution of 2 ml of methanol and 2 ml of THF, and 0.15 ml of a 1M aqueous sodium hydroxide solution was added thereto, followed by reaction at room temperature for 20 hours. To the reaction solution were added 0.15 ml of 1M hydrochloric acid and 20 ml of water, and the resulting precipitate was collected by filtration. The precipitate was washed with water and then dried to obtain 16 mg of 2-(4-azocan-1-yl-3-cyanophenyl) isonicotinic acid.

Preparation Example 6

(1) Under an argon atmosphere, 820 mg of 4-bromo-1-isobutoxy-2-nitrobenzene and 830 mg of bispinacolatodiboron were dissolved in toluene and the resulting solution was heated and refluxed for 15 hours in the presence of 60 mg of dichlorodi(triphenylphosphine)palladium, 50 mg of triphenylphosphine, and 350 mg of potassium acetate. After cooling to room temperature, 660 mg of methyl 5-bromothiophene-2-carboxylate, 150 mg of tetrakis(triphenylphosphine)palladium, and 7.5 ml of a 2M aqueous sodium carbonate solution were added to the solution, followed by heating at 100° C. for 6 hours. After cooling to room temperature, the solution was extracted with ethyl acetate and the resulting organic layer was dried and concentrated under reduced pressure. The residue was purified by silica gel column chromatography (hexane:ethyl acetate=90:10) to obtain 790 mg of methyl 5-(3-nitro-4-isobutoxyphenyl)thiophene-2-carboxylate.

(2) Then, 570 mg of the compound was dissolved in a mixed solution of 10 ml of ethanol and 10 ml of THF, and 3 ml of a 1M aqueous sodium hydroxide solution was added thereto, followed by heating at 60° C. for 18 hours. After cooling to room temperature, the resulting solution was diluted with water and ethyl acetate and an aqueous layer was separated. The aqueous layer was neutralized with 1M hydrochloric acid and then extracted with ethyl acetate. The resulting organic layer was dried and concentrated under reduced pressure to obtain 350 mg of 5-(3-nitro-4-isobutoxyphenyl)thiophene-2-carboxylic acid.

Preparation Example 7

(1) Using (3-cyano-4-isobutoxyphenyl)boronic acid and methyl 4,5-dibromo-3-fluorothiophene-2-carboxylate, methyl 4-bromo-5-(3-cyano-4-isobutoxyphenyl)-3-fluorothiophene-2-carboxylate was obtained in accordance with the method of Preparation Example 1(1). To an ethanol (60 ml) suspension of 1.75 g of the compound was added 1.00 g of 10% palladium-carbon, followed by stirring at room temperature for 4 hours under a hydrogen atmosphere at normal pressure. After insoluble matter was removed by filtration, the filtrate was concentrated under reduced pressure and the residue was purified by silica gel column chromatography (hexane:ethyl acetate=10:1 to 5:1) to obtain 0.39 g of methyl 5-(3-cyano-4-isobutoxyphenyl)-3-fluorothiophene-2-carboxylate.

(2) The compound was dissolved in 15 ml of THF, and 2.5 ml of a 1M aqueous sodium hydroxide solution was added thereto, followed by heating at 60° C. for 5 hours. After cooling to room temperature, 2.5 ml of 1M hydrochloric acid and water were added thereto, followed by extraction with ethyl acetate. The resulting organic layer was dried and concentrated under reduced pressure. The resulting solid was recrystallized from ethyl acetate and hexane to obtain 252 mg of 5-(3-cyano-4-isobutoxyphenyl)-3-fluorothiophene-2-carboxylic acid.

(3) Then, 215 mg of sodium hydroxide was added to an ethanol (60 ml) solution of 1.81 g of 5-(3-cyano-4-isobutoxyphenyl)-3-fluorothiophene-2-carboxylic acid, followed by stirring at 80° C. overnight. After the reaction solution was cooled to room temperature, the precipitate was collected by filtration to obtain 1.60 g of sodium 5-(3-cyano-4-isobutoxyphenyl)-3-fluorothiophene-2-carboxylate.

Preparation Example 8

(1) 87 mg of tetrakis(triphenylphosphine)palladium was added to a toluene (25 ml) suspension of 966 mg of methyl 2-(3-cyano-4-{[(trifluoromethyl)sulfonyl]oxy}phenyl)isonicotinate, 610 mg of phenylboronic acid and 518 mg of potassium carbonate, followed by heating at 100° C. in an argon atmosphere for 2 hours. Water was added to the reaction mixture, followed by extraction with ethyl acetate. The organic layer was washed with brine, dried and concentrated under reduced pressure. The residue was purified by silica gel column chromatography (hexane:ethyl acetate=95:5 to 70:30) to obtain 758 mg of methyl 2-(2-cyanobiphenyl-4-yl)isonicotinate.

(2) 758 mg of this compound was dissolved in a mixture of 10 ml of methanol and 10 ml of THF, and 7.2 ml of aqueous 1 M sodium hydroxide solution was added thereto, followed by heating at 60° C. for 13 hours. The reaction mixture was cooled to room temperature, neutralized with 1 M hydrochloric acid, and concentrated under reduced pressure. The residue was recrystallized from a mixture of ethanol and water to obtain 472 mg of 2-(2-cyanobiphenyl-4-yl)isonicotinic acid.

(3) 414 mg of this compound was dissolved in 15 ml of ethanol, and 1.5 ml of aqueous 1 M sodium hydroxide solution was added thereto, followed by stirring at room temperature for 30 minutes. The reaction solution was concentrated under reduced pressure to obtain 430 mg of sodium 2-(2-cyanobiphenyl-4-yl)isonicotinate.

Preparation Example 9

(1) 212 mg of methyl 2-(3-cyano-4-fluorophenyl)isonicotinate and 68 mg of pyrazole were dissolved in 4 ml of DMSO, and 102 mg of potassium tert-butoxide was added, followed by stirring at room temperature for 30 minutes. The reaction mixture was diluted with water, and extracted with ethyl acetate. The organic layer was washed with brine, dried and concentrated under reduced pressure. The resulting residue was purified by silica gel column chromatography (hexane:ethyl acetate=67:33) to obtain 251 mg of methyl 2-[3-cyano-4-(1H-pyrazol-1-yl)phenyl]isonicotinate.

(2) 236 mg of this compound was dissolved in a mixture liquid of 10 ml of methanol and 5 ml of THF, and 1.16 ml of aqueous 1 M sodium hydroxide solution was added, followed by heating at 80° C. for 40 minutes. The reaction liquid was cooled to room temperature, washed with water, and the organic solvent was evaporated away under reduced pressure. The reaction liquid was washed with diethyl ether to obtain an aqueous layer. The aqueous layer was neutralized with 1 M hydrochloric acid, followed by extraction with ethyl acetate. The organic layer was washed with brine, dried and concentrated under reduced pressure, and the resulting residue was recrystallized from a mixture of ethanol and water to obtain 103 mg of 2-[3-cyano-4-(1H-pyrazol-1-yl)phenyl]isonicotinic acid.

(3) 92 mg of this compound was dissolved in ethanol, and 0.317 ml of aqueous 1 M sodium hydroxide solution was added thereto, followed by stirring at room temperature for 15 minutes. The reaction liquid was concentrated, the residue was suspended in 2-propanol, and the precipitate was collected by filtration to obtain 93 mg of sodium 2-[3-cyano-4-(1H-pyrazol-1-yl)phenyl]isonicotinate.

Preparation Example 10

(1) 1.32 g of methyl 2-[4'-(benzyloxy)-2,3'-dicyanobiphenyl-4-yl]isonicotinate, which had been obtained in the same manner as in Preparation Example 8(1) using 4-(benzyloxy)-3-cyanophenyl]boric acid and methyl 2-(3-cyano-4-{[(trifluoromethyl)sulfonyl]oxy}phenyl)isonicotinate, was dissolved in a mixture of 50 ml of THF and 50 ml of methanol, and 0.5 g of palladium-carbon was added, followed by stirring in a hydrogen atmosphere at room temperature for 12 hours. The reaction mixture was filtered, and the filtrate was concentrated under reduced pressure to obtain 0.5 g of methyl 2-(2,3'-dicyano-4'-hydroxybiphenyl-4-yl)isonicotinate.

(2) 230 mg of this compound was dissolved in DMF, and 50 µL of iodomethane and 108 mg of potassium carbonate were added, followed by stirring at room temperature for 2 hours. Water was added to the reaction mixture, followed by extraction with ethyl acetate. The organic layer was washed with brine, dried and concentrated under reduced pressure. Chloroform was added to the residue, and the precipitated crystal was collected by filtration, followed by washing with chloroform to obtain 73 mg of methyl 2-(2,3'-dicyano-4'-methoxybiphenyl-4-yl)isonicotinate.

(3) 73 mg of this compound was dissolved in 2 ml of methanol and 2 ml of THF, and 220 µL of an aqueous 1 M sodium hydroxide solution was added, followed by heating at 60° C. for 2 hours. After cooling, the solvent was removed under reduced pressure, and then water was added to the residue, followed by neutralization with 1 M hydrochloric acid. The precipitated crystal was collected by filtration and washed with a mixture of ethanol and water to obtain 64 mg of 2-(2,3'-dicyano-4'-methoxybiphenyl-4-yl)isonicotinic acid.

Preparation Example 11

(1) 58 mg of tetrakis(triphenylphosphine)palladium and 208 mg of potassium carbonate were added to a toluene (10 ml) solution of 386 mg of methyl 2-(3-cyano-4-{[(trifluoromethyl)sulfonyl]oxy}phenyl)isonicotinate and 534 mg of 1-(triisopropylsilyl)pyrrole-3-boronic acid, then this was irradiated with microwaves and heated at 130° C. in a nitrogen atmosphere for 1 hour. Water was added to the reaction mixture, followed by extraction with ethyl acetate. The organic layer was washed with brine, dried and concentrated under reduced pressure. The residue was purified by silica gel column chromatography (hexane:ethyl acetate=95:5 to 70:30) to obtain 24 mg of methyl 2-{3-cyano-4-[1-(triisopropylsilyl)-1H-pyrrol-3-yl]phenyl}isonicotinate.

(2) 24 mg of this compound was dissolved in 1 ml of THF, and 63 µL of 1 M tetrabutylammonium fluoride/THF solution was added thereto, followed by stirring at room temperature for 15 hours. The reaction mixture was concentrated under reduced pressure, and the residue was purified by silica gel column chromatography (hexane:ethyl acetate=90:10 to 70:30) to obtain 6 mg of methyl 2-[3-cyano-4-(1H-pyrrol-3-yl)phenyl]isonicotinate.

(3) 6 mg of this compound was dissolved in a mixture of 0.5 ml of methanol and 0.5 ml of THF, and 22 µl of aqueous 1 M sodium hydroxide solution was added, followed by heating at 60° C. for 2 hours. The reaction liquid was cooled, and the solvent was removed under reduced pressure. Water was added to the residue, followed by neutralization with 1 M hydrochloric acid. The precipitated crystal was collected by filtration and washed with a mixture of ethanol and water to obtain 1.5 mg of 2-[3-cyano-4-(1H-pyrrol-3-yl)phenyl]isonicotinic acid.

Preparation Example 12

(1) 131 mg of methyl 2-(4-amino-3-cyanophenyl)isonicotinate and 67 µl of 2,5-dimethoxytetrahydrofuran were dissolved in 1.3 ml of acetic acid solution, followed by heating and stirring at 100° C. for 4 hours. The solution was poured into water, followed by extraction with ethyl acetate. The solvent of the organic layer was evaporated under reduced pressure, and the residue was purified by column chromatography (hexane:ethyl acetate=10:1 to 1:1) to obtain 100 mg of methyl 2-[3-cyano-4-(1H-pyrrol-1-yl)phenyl]isonicotinate.

(2) 100 mg of methyl 2-[3-cyano-4-(1H-pyrrol-1-yl)phenyl]isonicotinate was dissolved in a mixture of 2 ml of methanol and 3 ml of THF, and 66 µl of aqueous 1 M sodium hydroxide solution was added, followed by heating under reflux for 3 hours. The reaction mixture was cooled, then neutralized with 66 µl of 1 M hydrochloric acid, followed by extraction with a mixture of 2-propanol and chloroform (1:4). The organic layer was washed with brine. The solvent of the organic layer was evaporated under reduced pressure, and the resulting residue was recrystallized from a mixture of 2-propanol and chloroform (1:4) to obtain 95 mg of 2-[3-cyano-4-(1H-pyrrol-1-yl)phenyl]isonicotinic acid.

Preparation Example 13

(1) A toluene (0.5 ml) suspension of 20 mg of methyl 5-(3-cyano-4-{[(trifluoromethyl)sulfonyl]oxy}phenyl)thiophene-2-carboxylate and 10 mg of potassium carbonate was added to 15 mg of 3-aminobenzeneboronic acid monohydrate, and in an argon atmosphere, 8 mg of tetrakis(triphenylphosphine)palladium was added thereto. The mixture was stirred overnight at 100° C., then cooled to room temperature, and filtered through Celite. The solvent was evaporated under reduced pressure to obtain methyl 5-(3'-amino-2-cyanobiphenyl-4-yl)thiophene-2-carboxylate.

(2) 0.2 ml of aqueous 1 M sodium hydroxide solution was added to a methanol (0.25 ml)/tetrahydrofuran (0.25 ml) solution of methyl 5-(3'-amino-2-cyanobiphenyl-4-yl)thiophene-2-carboxylate, followed by stirring overnight at 60° C. 1 M hydrochloric acid was added to the reaction liquid to make it acidic, and the solvent was evaporated under reduced pressure. The residue was purified by HPLC [elution through column: SunFire (registered trademark) C18 5 µm, 19 mm×100 mm, solvent: MeOH/aqueous 0.1% formic acid solution=10/90 for 1 minute, ratio change to 95/5, taking 8 minutes, and further elution with 95/5 for 3 minutes, flow rate: 25 mL/min), thereby obtaining 2.5 mg of 5-(3'-amino-2-cyanobiphenyl-4-yl)thiophene-2-carboxylic acid.

Preparation Example 14

In the same manner as in Preparation Example 13 but using 25 mg of {4-[(tert-butoxycarbonyl)amino]-3-fluorophenyl}boronic acid in place of 3-aminobenzeneboronic acid monohydrate, 5-{4'-[(tert-butoxycarbonyl)amino]-2-cyano-3'-fluorobiphenyl-4-y;}thiophene-2-carboxylic acid was obtained. The compound was dissolved in a mixed solvent of 0.5 ml of dichloromethane and 0.5 ml of trifluoroacetic acid, followed by stirring at room temperature for 2 hours. The reaction liquid was evaporated under reduced pressure, and then purified in the same manner as that for the purification treatment in Example 13 to obtain 9.2 mg of 5-(4'-amino-2-cyano-3'-fluorobiphenyl-4-yl)thiophene-2-carboxylic acid.

Preparation Example 15

(1) 6 ml of aqueous 2 M sodium carbonate solution and 70 mg of tetrakistriphenylphosphine palladium were added to a toluene (15 ml) solution of 450 mg of (3-cyano-4-pyridin-3-ylphenyl)boronic acid and 412 mg of Methyl 2-chloroisonicotinate acid, and in an argon atmosphere, this was heated at 100° C. for 2 hours. 3 ml of ethanol was added, followed by further heating at 100° C. for 1 hour. Water was added to the reaction mixture, followed by extraction with chloroform.

The organic layer was washed with brine, dried and concentrated under reduced pressure.

The residue was purified by silica gel column chromatography (chloroform:methanol=99:1 to 93:7) to obtain 127 mg of ethyl 2-(3-cyano-4-pyridin-3-ylphenyl)isonicotinate. F: 330.

(2) 100 mg of this compound was dissolved in a mixture of 10 ml of methanol and 3 ml THF, and 3 ml of aqueous 1 M sodium hydroxide solution was added thereto and heated at 60° C. for 1.5 hours. After cooled to room temperature, the reaction mixture was made to have pH of 3 to 4 with 1 M hydrochloric acid added thereto, and then concentrated under reduced pressure. The residue was washed with a mixture of ethanol and water to obtain 54 mg of 2-(3-cyano-4-pyridin-3-ylphenyl)isonicotinic acid 0.3 hydrochloride.

Preparation Example 16-269

In the same manner as in Preparation Examples 1 to 15 but starting from the corresponding starting compounds, the compounds of Preparation Examples 16 to 269 shown in Tables 3 to 20 below were produced. The structures and the physicochemical data of the compounds of Preparation Examples 1 to 269 are shown in Tables 3 to 20.

Thus produced, the compounds of formula (I) that are the active ingredient of the pharmaceutical composition of the present invention may be formed into pharmaceutical compositions according to the following formulation.

Formulation Example 100 g of an active ingredient is taken and mixed with 652 g of lactose and 163 g of corn starch. The mixture is, as combined with 300 g of an aqueous solution of 10% hydroxypropyl cellulose (for example, Nippon Soda's HPC-SL), granulated and dried using a fluidized layer granulator. The dried product is mixed with 50 g of low-substitution hydroxypropyl cellulose (for example, Shin-etsu Chemical's L-HPC), and further mixed with 5 g of magnesium stearate to prepare a mixture powder for tabletting. Using a rotary tabletting machine (for example, by Kikusui) with a tabletting mallet having a diameter of 8 mm and a mortar, the mixture powder is tabletted into tablets of 200 mg each.

TABLE 1

| REx | Str | Dat |
|---|---|---|
| 27 | 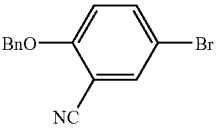 | EI: 287, 289 |
| 28 | 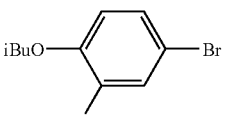 | F: 298 |
| 29 | 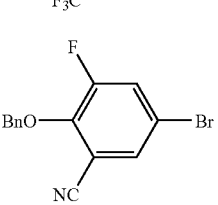 | EI: 215, 217 |

TABLE 1-continued

| REx | Str | Dat |
|---|---|---|
| 30 | 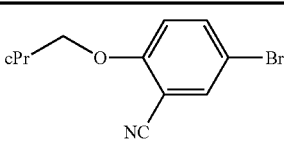 | F: 252 |
| 31 | 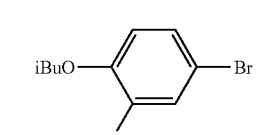 | F: 274, 276 |
| 32 | 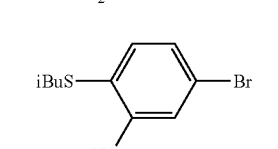 | EI: 269, 271 |
| 33 | 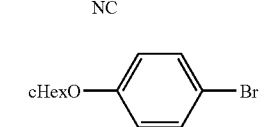 | EI: 279, 281 |
| 34 | 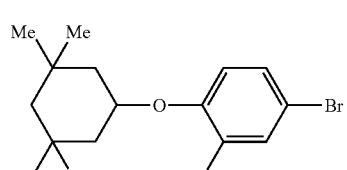 | F: 336, 338 |
| 35 | 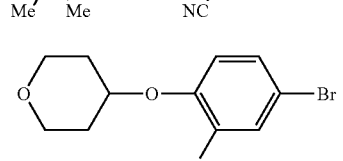 | F: 282, 284 |
| 36 | 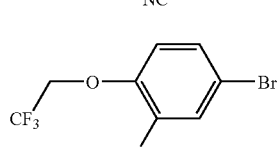 | EI: 279, 281 |
| 37 | 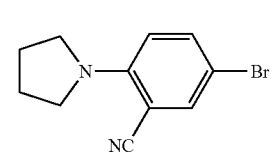 | F: 251 |
| 38 | 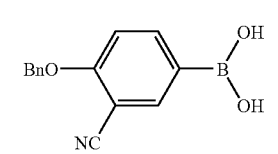 | ES: 254 |
| 39 | 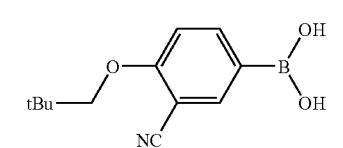 | FN: 232 |

TABLE 1-continued
| REx | Str | Dat |
|---|---|---|
| 40 | 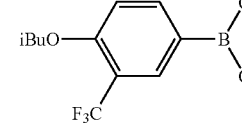 | FN: 261 |
| 41 | 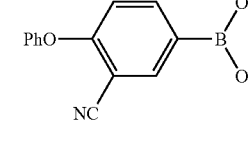 | F: 296 (G-2W) |
| 42 | 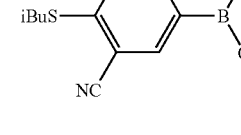 | F: 235 |
| 43 | 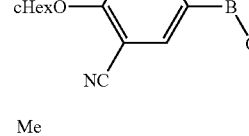 | FN: 244 |
| 44 | 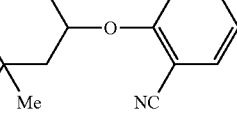 | F: 358 (F-2W) |
| 45 | 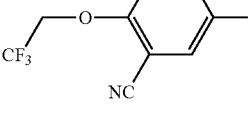 | F: 302 (G-2W) |
| 46 | 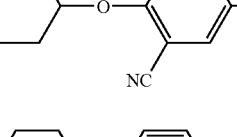 | F: 304 (G-2W) |
| 47 | 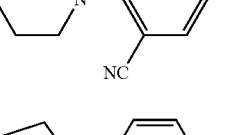 | ES: 231 |
| 48 | 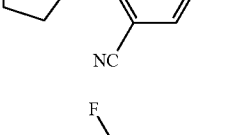 | ES: 217 |
| 49 | 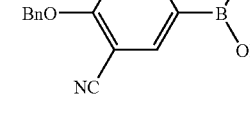 | F: 328 (G-2W) |
| 50 | 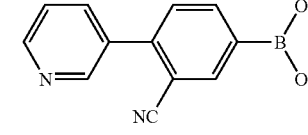 | F: 281 (G-2W) |
TABLE 2
| REx | Str | Dat |
|---|---|---|
| 51 | 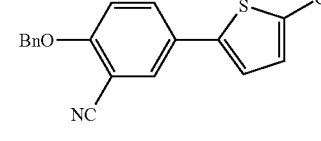 | F: 350 |
| 52 | 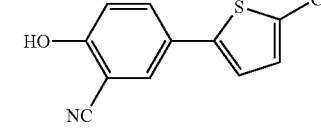 | FN: 258 |
| 53 | 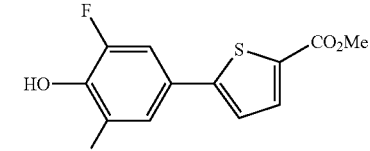 | FN: 276 |
| 54 | 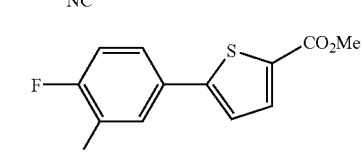 | F: 262 |
| 55 | 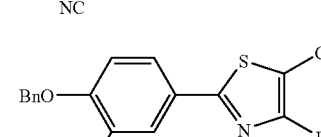 | AP: 401(Na) |
| 56 | 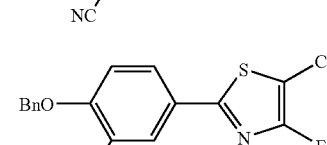 | APN: 287 |
| 57 | 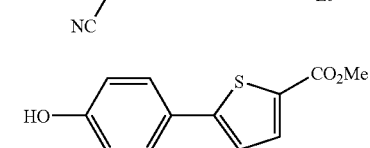 | APN: 259 |
| 58 | 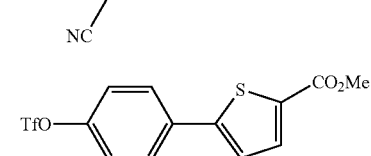 | F: 392 |

TABLE 2-continued

| REx | Str | Dat |
|---|---|---|
| 59 | TfO-phenyl(NC)-thiophene(Me)-CO2Et | F: 421 |
| 60 | TfO-phenyl(NC)-thiophene(Et)-CO2Me | AP: 443(Na) |
| 61 | TfO-phenyl(NC)-thiazole-CO2Me | AP: 415(Na) |
| 62 | TfO-phenyl(NC)-pyrazole-CO2Et | AP: 412(Na) |
| 63 | TfO-phenyl(NC)-isoxazole-CO2Et | AP: 413(Na) |
| 64 | TfO-phenyl(NC)-pyrazole(N-Me)-CO2Me | AP: 412(Na) |
| 65 | TfO-phenyl(NC)-isothiazole-CO2Et | AP: 429(Na) |

TABLE 3

A—X—[phenyl(R²)]—[pyridine]—COOH

| Ex | Syn | A—X— | R² | Dat |
|---|---|---|---|---|
| 1 | 1 | iBuO— | CN | F: 297; NMR: 4.00(2 H, d), 7.38(1 H, d), 7.77(1 H, dd) |
| 2 | 2 | iPrO— | CN | F: 283; NMR: 1.36(6 H, d), 7.41(1 H, d), 8.83(1 H, d) |
| 3 | 3 | MeS—(CH₂)₃—O— | CN | F: 329; NMR: 4.31(2 H, t), 7.40(1 H, d), 8.83(1 H, d) |
| 16 | 1 | BnO— | CN | F: 331; NMR: 5.34(2 H, s), 7.71(1 H, d), 8.39(1 H, d) |
| 17 | 1 | piperidin-1-yl | CN | F: 308; NMR: 3.20-3.28(4 H, m), 7.24(1 H, d), 7.75(1 H, dd) |
| 18 | 1 | pyrrolidin-1-yl | CN | F: 294; NMR: 3.53-3.69(4 H, m), 6.88(1 H, d), 7.67(1 H, dd) |
| 19 | 1 | tBu—CH₂—O— | CN | F: 311; NMR: 3.89(2 H, s), 7.37(1 H, d), 8.83(1 H, d) |
| 20 | 1 | CF₃—CH₂—O— | CN | F: 323; NMR: 5.09(2 H, q), 7.53(1 H, d), 7.80(1 H, dd) |
| 12 | 1 | tetrahydropyran-4-yl-O— | CN | F: 325; NMR: 3.82-3.94(2 H, m), 7.49(1 H, d), 7.77(1 H, dd) |
| 22 | 2 | cPenO— | CN | F: 309; NMR: 5.10(1 H, m), 7.38(1 H, d), 8.83(1 H, d) |
| 23 | 2 | iPenO— | CN | ES: 311; NMR: 4.25(2 H, t), 7.41(1 H, d), 8.83(1 H, d) |
| 24 | 2 | EtO— | CN | F: 269; NMR: 1.41(3 H, t), 7.37(1 H, d), 8.83(1 H, d) |
| 25 | 2 | nBuO— | CN | F: 297; NMR: 4.23(2 H, t), 7.39(1 H, d), 8.83(1 H, d) |
| 26 | 2 | pyrrol-1-yl-CH₂CH₂-O— | CN | F: 334; NMR: 6.01(2 H, t), 7.33(1 H, d), 8.83(1 H, d) |
| 27 | 2 | nPrO— | CN | F: 283; NMR: 4.19(2 H, t), 7.38(1 H, d), 7.77(1 H, dd) |

TABLE 3-continued

A—X—[phenyl(R²)]—[pyridine-COOH]

| Ex | Syn | A—X— | R² | Dat |
|----|-----|------|-----|-----|
| 28 | 2 | 2Py—CH₂—O— | CN | F: 332; NMR: 5.45(2 H, s), 8.35(1 H, s), 8.82(1 H, d) |
| 29 | 2 | 3Py—CH₂—O— | CN | F: 332; NMR: 5.43(2 H, s), 8.36(1 H, s), 8.83(1 H, s) |
| 30 | 2 | iBuO— | CF₃ | F: 340; NMR: 3.98(2 H, d), 7.37(1 H, d), 7.76(1 H, dd) |
| 31 | 2 | MeO— | CN | F: 255; NMR: 4.00(3 H, s), 7.39(1 H, d), 7.77(1 H, dd) |
| 32 | 2 | nPenO— | CN | F: 311; NMR: 4.22(2 H, t), 7.38(1 H, d), 7.77(1 H, dd) |
| 33 | 2 | nHexO— | CN | F: 325; NMR: 4.21(2 H, t), 7.37(1 H, d), 7.77(1 H, dd) |
| 34 | 2 | (Et)₂CHCH₂O— | CN | F: 325; NMR: 4.13(2 H, d), 7.41(1 H, d), 7.77(1 H, dd) |
| 35 | 2 | MeO(CH₂)₃O— | CN | F: 313; NMR: 3.53(2 H, t), 7.39(1 H, d), 7.77(1 H, dd) |
| 36 | 2 | (Et)₂CHO— | CN | F: 311; NMR: 0.95(6 H, t), 7.41(1 H, d), 7.77(1 H, dd) |
| 37 | 2 | PhOCH₂CH₂O— | CN | F: 361; NMR: 4.34-4.43(2 H, m), 7.31(2 H, t), 7.78(1 H, dd) |

TABLE 4

| Ex | Syn | A—X— | R² | Dat |
|----|-----|------|-----|-----|
| 38 | 2 | MeOCH₂CH₂O— | CN | F: 299; NMR: 3.36(3 H, s), 7.41(1 H, d), 7.77(1 H, dd) |
| 39 | 2 | 4-NC-C₆H₄-CH₂-O— | CN | F: 356; NMR: 7.46(1 H, d), 7.78(1 H, dd), 7.94(2 H, d) |
| 40 | 2 | 6-fluoro-chroman-8-yl-O-CH₂CH₂-O— | CN | F: 435; NMR: 6.52(1 H, dd), 7.48(1 H, d), 7.78(1 H, dd) |
| 41 | 2 | NC—(CH₂)₃—O— | CN | F: 308; NMR: 2.70(2 H, t), 7.42(1 H, d), 7.78(1 H, dd) |
| 42 | 2 | cHex-CH₂—O— | CN | F: 337; NMR: 4.03(2 H, d), 7.37(1 H, d), 7.77(1 H, dd) |
| 43 | 2 | HO₂C—CH₂—O— | CN | F: 299; NMR: 4.99(2 H, s), 7.29(1 H, d), 7.77(1 H, dd) |
| 44 | 2 | H₂N(OC)CH₂O— | CN | F: 298; NMR: 4.77(2 H, s), 7.21(1 H, d), 7.77(1 H, dd) |
| 45 | 2 | BnO—(CH₂)₃—O— | CN | F: 389; NMR: 4.51(2 H, s), 7.39(1 H, d), 7.77(1 H, dd) |
| 46 | 2 | (tetrahydrofuran-2-yl)-CH₂-O— | CN | F: 325; NMR: 3.71(1 H, q), 7.40(1 H, d), 7.77(1 H, dd) |
| 47 | 2 | cHexO— | CN | F: 323; NMR: 4.65-4.74(1 H, m), 7.43(1 H, d), 7.75 (1 H, dd) |
| 48 | 2 | (Me)₂N(CO)CH₂O— | CN | F: 326; NMR: 2.86(3 H, s), 7.24(1 H, d), 7.77(1 H, d) |
| 49 | 2 | pHO— | CN | F: 317; NMR: 7.25(2 H, d), 7.52(2 H, t), 7.80(1 H, d) |
| 50 | 2 | 3-NC-C₆H₄-CH₂-O— | CN | F: 356; NMR: 5.43(2 H, s), 7.46(1 H, d), 8.58(1 H, d) |
| 51 | 2 | 3,3,5,5-tetramethylcyclohexyl-O— | CN | FN: 377; NMR: 4.86-4.96(1 H, m), 7.42(1 H, d), 8.83 (1 H, d) |

TABLE 5
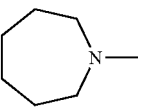
| Ex | Syn | A—X— | Sal | Dat |
|---|---|---|---|---|
| 4 | 4 | 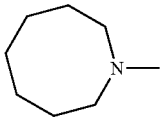 | HCl | F: 322; NMR: 3.71(4 H, dd), 7.09(1 H, d), 8.20(1 H, dd) |
| 5 | 5 | 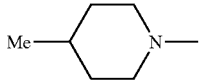 | | F: 336; NMR: 3.78(4 H, dd), 7.07(1 H, d), 7.68(1 H, dd) |
| 52 | 4 | cHex-CH$_2$—NH— | Na | F: 358(Na); NMR: 3.09(2 H, dd), 6.87(1 H, d), 7.58(1 H, dd) |
| 53 | 1 | iBuS— | Na | F: 335(Na); NMR: 3.07(2 H, d), 7.65-7.70(2 H, m), 8.24(1 H, s) |
| 54 | 2 | cBu—CH$_2$—O— | Na | F: 309; NMR: 4.19(2 H, d), 7.36(1 H, d), 7.66(1 H, dd) |
| 55 | 4 | 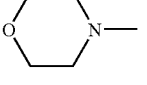 | HCl | F: 322; NMR: 0.98(3 H, d), 7.78(1 H, dd), 8.43(1 H, d) |
| 56 | 5 | 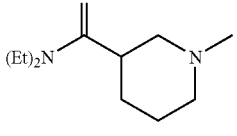 | | FN: 308; NMR: 3.79(4 H, dd), 7.28(1 H, d), 7.76(1 H, dd) |
| 57 | 5 | 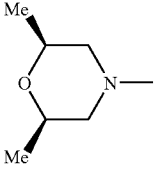 | | F: 407; NMR: 1.01(3 H, t), 7.27(1 H, d), 7.75(1 H, dd) |
| 58 | 5 | 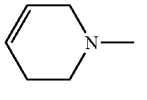 | | F: 338; NMR: 1.16(6 H, d), 7.26(1 H, d), 7.76(1 H, dd) |
| 59 | 5 | 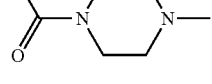 | | F: 306; NMR: 5.79-5.96(2 H, m), 7.24(1 H, d), 7.74(1 H, dd) |
| 60 | 5 | 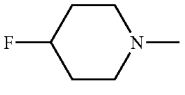 | | F: 381; NMR: 1.22(3 H, t), 7.28(1 H, d), 8.83(1 H, d) |
| 61 | 4 |  | Na | F: 326; NMR: 3.19-3.28(2 H, m), 7.28(1 H, d), 7.65(1 H, dd) |
| 62 | 4 | nPr—NH— | Na | F: 304(Na); NMR: 3.20(2 H, dt), 6.37, (1 H, t), 6.88(1 H, d) |

TABLE 5-continued

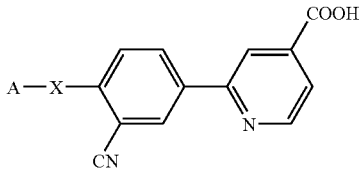

| Ex | Syn | A—X— | Sal | Dat |
|---|---|---|---|---|
| 63 | 4 | 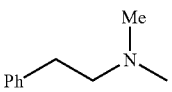 | Na | F: 380(Na); NMR: 3.68(2 H, dd), 7.13(1 H, d), 7.60(1 H, d) |

TABLE 6

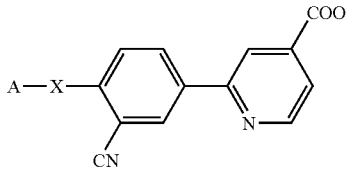

| Ex | Syn | A—X— | Sal | Dat |
|---|---|---|---|---|
| 64 | 4 | iBu-NH— | Na | F: 318 (Na); NMR: 3.07 (2H, dd), 6.39 (1H, t), 6.88 (1H, d) |
| 65 | 4 | cPen-NH— | Na | F: 330 (Na); NMR: 3.87-3.99 (1H, m), 5.96 (1H, d), 6.92 (1H, d) |
| 66 | 4 | nBu—NH— | Na | F: 318 (Na); NMR: 3.23 (2H, dt), 6.87 (1H, d), 7.58 (1H, d) |
| 67 | 4 | nBu—N(Me)— | Na | F: 332 (Na); NMR: 3.45 (2H, dd), 7.11 (1H, d), 7.60 (1H, dd) |
| 68 | 4 | 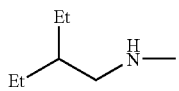 | Na | F: 346 (Na); NMR: 3.14 (2H, dd), 6.87 (1H, d), 7.58 (1H, dd) |
| 69 | 4 | 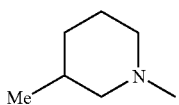 | Na | F: 322; NMR: 2.81 (1H, dt), 7.22 (1H, d), 7.64 (1H, dd) |
| 70 | 4 | nHex-N(Me)— | Na | F: 338; NMR: 3.44 (2H, dd), 7.09 (1H, d), 7.62 (1H, dd) |
| 71 | 4 | cOct-NH— | Na | F: 350; NMR: 3.65-3.76 (1H, m), 6.86 (1H, d), 7.56 (1H, dd) |
| 72 | 4 | cHex-NH— | Na | F: 322; NMR: 3.40-3.53 (1H, m), 6.93 (1H, d), 7.59 (1H, dd) |
| 73 | 4 | cHep-NH— | Na | F: 336; NMR: 3.61-3.72 (1H, m), 6.85 (1H, d), 7.58 (1H, dd) |
| 74 | 4 | nPen-CH(Me)—NH— | Na | F: 338; NMR: 3.61-3.72 (1H, m), 6.89 (1H, d), 7.59 (1H, dd) |
| 75 | 4 | nBu—N(Et)- | Na | F: 346 (Na); NMR: 3.47 (2H, q), 7.13 (1H, d), 7.61 (1H, dd) |
| 76 | 4 | 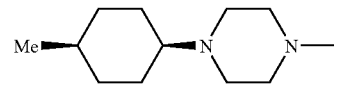 | | APN: 403; NMR: 0.94 (3H, d), 7.31 (1H, d), 8.83 (1H, d) |
| 77 | 4 | 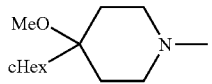 | | APN: 418; NMR: 3.09 (3H, s), 7.74 (1H, dd), 8.43 (1H, d) |
| 78 | 4 | 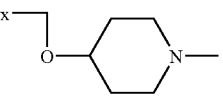 | | APN: 418; NMR: 3.26 (2H, d), 7.26 (1H, d), 8.44 (1H, d) |
| 79 | 4 | 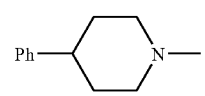 | | APN: 382; NMR: 3.79 (2H, d), 7.27 (1H, d), 8.83 (1H, dd) |

TABLE 6-continued

| Ex | Syn | A—X— | Sal | Dat |
|---|---|---|---|---|
| 80 | 4 | (N-methylisoindoline) | | APN: 340; NMR: 5.08 (4H, s), 7.03 (1H, d), 7.69 (1H, dd) |
| 81 | 2 | (2-cyanobenzyl-O—) | Na | F: 356; NMR: 5.51 (2H, s), 7.97 (1H, d), 8.57 (1H, d) |
| 82 | 2 | (Me)₂C=CHCH₂—O— | Na | F: 309; NMR: 5.49 (1H, t), 7.37 (1H, d), 7.66 (1H, d) |

TABLE 7

| Ex | Syn | Str | Dat |
|---|---|---|---|
| 83 | 1 | iBuO, NC, F, CO₂H | F: 315; NMR: 4.02 (2H, d), 7.42 (1H, d), 8.63 (1H, d) |
| 84 | 1 | iBuO, NC, CO₂H, F | F: 315; NMR: 4.00 (2H, d), 7.37 (1H, d), 8.31 (1H, d) |
| 85 | 1 | iBuO, NC, CO₂H, Cl | F: 331; NMR: 4.00 (2H, d), 7.37 (1H, d), 8.80 (1H, s) |
| 86 | 2 | Br, iBuO, NC, CO₂H | FN: 375; NMR: 4.04 (2H, d), 7.83 (1H, dd), 8.46 (1H, s) |
| 87 | 2 | Cl, iBuO, NC, CO₂H | FN: 329; NMR: 4.05 (2H, d), 7.84 (1H, dd), 8.47 (1H, s) |

TABLE 7-continued

| Ex | Syn | Str | Dat |
|---|---|---|---|
| 88 | 2 | 3-Br, 4-nPrO, 5-NC phenyl - pyridine - CO2H | F: 361; NMR: 4.20 (2H, t), 7.84 (1H, dd), 8.61 (1H, dd) |
| 89 | 1 | 3-Cl, 4-iBuO, ... pyridine - CO2Na | F: 331; NMR: 3.99 (2H, d), 7.13 (1H, d), 7.34 (1H, d) |
| 90 | 2 | 3-Br, 4-(2-ethylbutoxy), 5-NC phenyl - pyridine - CO2Na | F: 405; NMR: 4.12 (2H, d), 7.73 (1H, d), 8.45 (1H, d) |
| 91 | 2 | 3-F, 4-iBuO, 5-NC phenyl - pyridine - CO2Na | FN: 313; NMR: 4.13 (2H, d), 7.69 (1H, dd), 8.60 (1H, dd) |

TABLE 8

A—X— substituted phenyl (R¹, R²) — thiophene — COOH

| Ex | Syn | A—X— | R¹ | R² | Sal | Dat |
|---|---|---|---|---|---|---|
| 6 | 6 | iBuO— | H | NO₂ | | FN: 320; NMR: 3.99 (2H, d), 7.43 (1H, d), 7.62 (1H, d) |
| 92 | 2 | nPrO— | H | CN | Na | F: 310 (Na); NMR: 4.12 (2H, t), 7.16 (1H, d), 7.85 (1H, dd) |
| 93 | 1 | iBuO— | H | CN | | FN: 300; NMR: 3.98 (2H, d), 7.31 (1H, d), 7.59 (1H, d) |
| 94 | 5 | (N-methylazepanyl) | H | CN | Na | FN: 325; NMR: 1.51-1.57 (2H, m), 3.62 (2H, dd), 7.00 (1H, d) |
| 95 | 4 | nBu—N(Me)— | H | CN | Na | F: 337; NMR: 2.96 (3H, s), 7.23 (1H, d), 7.79 (1H, d) |
| 96 | 1 | iBu—S— | H | CN | Na | F: 340 (Na); NMR: 3.02 (1H, d), 7.22 (1H, d), 7.85 (1H, dd) |
| 97 | 2 | EtO—(CH₂)₂—O— | H | CN | | F: 318; NMR: 1.13 (3H, t), 7.92 (1H, dd), 8.07 (1H, d) |
| 98 | 2 | cBu—CH₂—O— | H | CN | | F: 314; NMR: 4.17 (2H, d), 7.58 (1H, d), 8.15 (1H, d) |
| 99 | 2 | MeO— | H | CN | | FN: 258; NMR: 3.97 (3H, s), 7.60 (1H, d), 8.18 (1H, d) |
| 100 | 2 | EtO— | H | CN | | FN: 272; NMR: 1.39 (3H, t), 7.59 (1H, d), 8.16 (1H, d) |
| 101 | 2 | iPrO— | H | CN | | F: 288; NMR: 1.32 (6H, d), 7.59 (1H, d), 8.15 (1H, d) |

TABLE 8-continued

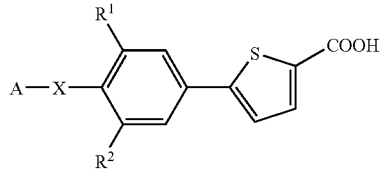

| Ex | Syn | A—X— | R¹ | R² | Sal | Dat |
|----|-----|------|----|----|-----|-----|
| 102 | 2 | iPenO— | H | CN | | F: 316;<br>NMR: 0.96 (6H, d), 7.59 (1H, d), 8.16 (1H, d) |
| 103 | 2 | nBuO— | H | CN | | F: 302;<br>NMR: 4.20 (2H, t), 7.60 (1H, d), 8.16 (1H, d) |
| 104 | 2 | cPenO— | H | CN | | F: 314;<br>NMR: 5.05-5.08 (1H, m), 7.59 (1H, d), 8.15 (1H, d) |
| 105 | 2 | cPenO— | H | CN | Na | AP: 335 (Na);<br>NMR: 1.50-2.05 (8H, m), 7.12-7.40 (3H, m), 7.78-8.03 (2H, m) |
| 106 | 2 | 3Py—CH₂—O— | H | CN | | F:337;<br>NMR: 5.40 (2H, d), 7.60 (1H, d), 8.20 (1H, d) |
| 107 | 2 | 4Py—CH₂—O— | H | CN | | ES: 337;<br>NMR: 5.44 (2H, s), 7.61 (1H, d), 8.23 (1H, d) |
| 108 | 2 | 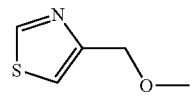 | H | CN | | F: 343;<br>NMR: 5.48 (2H, s), 7.60 (1H, d), 8.18 (1H, d) |

TABLE 9

| 109 | 2 | 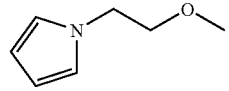 | H | CN | | F: 339;<br>NMR: 6.00 (2H, t), 7.59 (1H, d), 8.17 (1H, d) |
|-----|---|------|----|----|-----|-----|
| 110 | 2 | NC—(CH₂)₃—O— | H | CN | | FN: 311;<br>NMR: 4.27 (2H, t), 7.61 (1H, d), 8.19 (1H, d) |
| 111 | 1 | BnO— | H | CN | | FN: 334;<br>NMR: 5.36 (2H, s), 7.71 (1H, d), 8.19 (1H, d) |
| 112 | 1 | tBu—CH₂—O— | H | CN | | F: 316;<br>NMR: 3.85 (2H, s), 7.60 (1H, d), 8.16 (1H, d) |
| 113 | 1 | 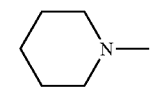 | H | CN | | F: 313;<br>NMR: 3.15-3.23 (4H, m), 7.18 (1H, d), 7.57 (1H, d) |
| 114 | 1 | 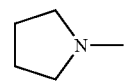 | H | CN | | F: 299;<br>NMR: 3.54-3.63 (4H, m), 6.84 (1H, d), 7.48 (1H, d) |
| 115 | 6 | cPr—CH₂—O— | H | CN | | F: 300;<br>NMR: 1.18-1.33 (1H, m), 7.59 (1H, d), 8.16 (1H, d) |
| 116 | 5 | 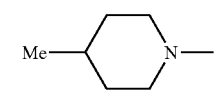 | H | CN | Na | FN: 325;<br>NMR: 0.97 (3H, d), 2.74-2.85 (2H, m), 7.31 (1H, d) |
| 117 | 2 | cPenO— | H | Ac | | FN: 329;<br>NMR: 2.55 (3H, s), 7.24 (1H, d), 7.50 (1H, d) |
| 118 | 1 | PhO— | H | CN | Na | FN: 320;<br>NMR: 6.97 (1H, d), 7.49 (2H, t), 7.87 (1H, dd) |
| 119 | 2 | cPen-O— | F | CN | | FN: 330;<br>NMR: 5.02-5.06 (1H, m), 7.17 (1H, d), 7.89 (1H, dd) |

TABLE 10

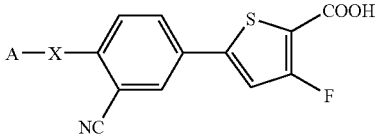

| Ex | Syn | A—X— | Sal | Dat |
|---|---|---|---|---|
| 7 | 7 | iBuO— | Na | F: 320; NMR: 1.10 (3H, d), 7.27 (1H, d), 7.31 (1H, s) |
| 120 | 7 | tBu—CH₂—O— | Na | F: 356 (Na); NMR: 3.83 (2H, s), 7.27 (1H, d), 7.29 (1H, s) |
| 121 | 7 | PhO— | Na | FN: 338; NMR: 6.96 (1H, d), 7.38 (1H, s), 7.49 (2H, t) |
| 122 | 7 | cHexO— | Na | FN: 344; NMR: 4.58-4.68 (1H, m), 7.30 (1H, s), 7.33 (1H, d) |
| 123 | 2 | nPrO— | | F: 306; NMR: 4.17 (2H, t), 7.34 (1H, d), 7.64 (1H, s) |
| 124 | 2 | cPenO— | | F: 332; NMR: 5.03-5.12 (1H, m), 7.34 (1H, d), 7.63 (1H, s) |
| 125 | 2 | cPenO— | Na | F: 332; NMR: 5.00-5.07 (1H, m), 7.28 (1H, d), 7.30 (1H, s) |
| 126 | 2 | cPr-CH₂—O— | | F: 318; NMR: 4.07 (2H, d), 7.32 (1H, d), 7.64 (1H, s) |
| 127 | 2 | EtO— | | F: 292; NMR: 4.26 (2H, q), 7.33 (1H, d), 7.64 (1H, s) |
| 128 | 2 | MeO— | | F: 278; NMR: 3.98 (3H, s), 7.34 (1H, d), 7.64 (1H, s) |
| 129 | 2 | iPenO— | | F: 334; NMR: 4.23 (2H, t), 7.36 (1H, d), 7.63 (1H, s) |
| 130 | 2 | cHex-CH₂—O— | Na | FN: 358; NMR: 3.98 (2H, d), 7.28 (1H, d), 7.31 (1H, s) |
| 131 | 2 | (Et)₂CHCH₂—O— | Na | F: 346; NMR: 4.07 (2H, d), 7.30 (1H, s), 7.85 (1H, dd) |
| 132 | 2 | 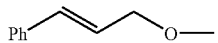 | Na | F: 380 (Na); NMR: 4.99 (2H, d), 7.65 (1H, s), 8.02 (1H, dd) |

TABLE 11

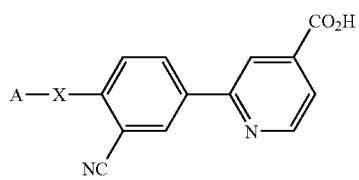

| Ex | Syn | A—X— | Sal | Dat |
|---|---|---|---|---|
| 8 | 8 | Ph— | Na | F: 301; NMR: 8.33 (1H, s), 8.55 (1H, dd), 8.64 (1H, d) |
| 9 | 9 | 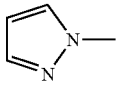 | Na | FN: 289; NMR: 6.67 (1H, t), 7.95 (1H, d), 8.66 (1H, d) |
| 10 | 10 | 4-MeO—3-CN—Ph— | | APN: 354; NMR: 4.01 (3H, s), 8.47 (1H, s), 8.87 (1H, d) |
| 11 | 11 | 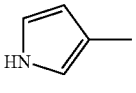 | | APN: 288; NMR: 7.84 (1H, d), 8.49 (1H, d), 8.79 (1H, d) |
| 12 | 12 | 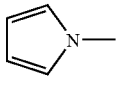 | | APN: 288; NMR: 6.39 (2H, t), 7.76 (1H, d), 8.50 (1H, s) |
| 15 | 15 | 3Py— | 0.3 HCl | ES: 302; NMR: 8.52 (1H, s), 8.60 (1H, dd), 8.93 (1H, d) |
| 133 | 8 | 4-F—Ph— | | FN: 317; NMR: 8.50 (1H, s), 8.46 (1H, dd), 8.92 (1H, d) |
| 134 | 8 | 3-MeO—Ph— | | FN: 329; NMR: 3.85 (3H, s), 7.86 (1H, dd), 8.54 (1H, dd) |
| 135 | 8 | 4-MeO—Ph— | Na | F: 331; NMR: 3.85 (3H, s), 7.12 (2H, d), 8.42 (1H, dd) |
| 136 | 8 | 4-Cl—Ph— | | FN: 333; NMR: 8.50(1H, s), 8.56 (1H, dd), 8.67 (1H, d) |
| 137 | 8 | 4-CF₃—Ph— | Na | FN: 367; NMR: 8.37 (1H, s), 8.51 (1H, dd), 8.67 (1H, d) |
| 138 | 8 | 2-MeO—Ph— | | F: 331; NMR: 3.80 (3H, s), 7.65 (1H, d), 8.91 (1H, d) |
| 139 | 8 | 4-Me—Ph— | Na | F: 315; NMR: 2.40 (3H, s), 7.37 (2H, d), 8.44 (1H, d) |
| 140 | 8 | 2Thie- | | F: 307; NMR: 7.29 (1H, dd), 8.49 (1H, s), 8.51 (1H, dd) |

TABLE 11-continued

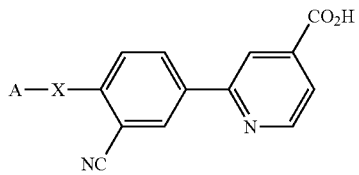

| Ex | Syn | A—X— | Sal | Dat |
|---|---|---|---|---|
| 141 | 8 | 3Thie- | Na | ES: 307; NMR: 7.57 (1H, dd), 8.34 (1H, s), 8.43 (1H, dd) |
| 142 | 8 | 3Fur- | | F: 291; NMR: 7.10 (1H, dd), 8.50 (1H, dd), 8.66 (1H, d) |
| 143 | 8 | 4-NC—Ph— | | FN: 324; NMR: 8.52 (1H, s), 8.59 (1H, dd), 8.92 (1H, d) |
| 144 | 8 | 4-HOOC—Ph— | | F: 345; NMR: 8.11 (2H, d), 8.59 (1H, dd), 8.92 (1H, d) |
| 145 | 8 | 2Fur | | FN: 289; NMR: 6.78 (1H, dd), 7.37 (1H, d), 8.57 (1H, dd) |
| 146 | 8 | 4-pyrazolyl (HN-N) | 0.3 HCl | FN: 289; NMR: 7.83 (1H, dd), 7.92 (1H, d), 8.89 (1H, d) |
| 147 | 8 | 4-iBuO—Ph— | | FN: 371; NMR: 1.01 (6H, s), 7.12 (2H, d), 8.51 (1H, dd) |
| 148 | 8 | 4-Et—Ph— | | FN: 327; NMR: 1.25 (3H, t), 7.41 (2H, d), 8.53 (1H, dd) |
| 149 | 8 | 3-Me—Ph— | | FN: 313; NMR: 2.42 (3H, s), 7.86 (1H, dd), 8.54 (1H, dd) |
| 150 | 8 | 2-Me—Ph— | | FN: 313; NMR: 2.19 (3H, s), 7.87 (1H, dd), 8.53 (1H, dd) |

TABLE 12

| Ex | Syn | A—X— | Sal | Dat |
|---|---|---|---|---|
| 151 | 8 | 3-Cl—Ph— | | Anal: Calc. C; 68.17%, H; 3.31%, N; 8.37%, Cl; 10.59% Found C; 67.90%, H; 3.51%, N; 8.23%, Cl; 10.43%; NMR: 8.51 (1H, s), 8.56 (1H, d), 8.92 (1H, d) |
| 152 | 8 | 2-Cl—Ph— | Na | FN: 333; NMR: 7.74 (1H, dd), 8.44 (1H, dd), 8.68 (1H, d) |
| 153 | 8 | 4-tBu—Ph— | Na | FN: 355; NMR: 1.35 (9H, s), 7.86 (1H, dd), 8.69 (1H, d) |
| 154 | 8 | 3,4-diMe-thiophene | | FN: 319; NMR: 2.17 (3H, s), 7.86 (1H, d), 8.92 (1H, d) |
| 155 | 8 | 4-HO—Ph— | | FN: 315; NMR: 6.94 (2H, d), 8.49 (1H, dd), 8.90 (1H, d) |
| 156 | 8 | 5-Me-2-thienyl | Na | FN: 319; NMR: 2.54 (3H, s), 7.54 (1H, d), 8.64 (1H, d) |
| 157 | 8 | 3,5-di(CF$_3$)—Ph— | | APN: 435; NMR: 8.30 (1H, s), 8.61 (1H, dd), 8.93 (1H, d) |
| 158 | 8 | 2Naph- | | APN: 349; NMR: 7.59-7.69 (2H, m), 8.61 (1H, dd), 8.93 (1H, d) |
| 159 | 8 | 2-benzothienyl | | APN: 367; NMR: 8.03 (1H, s), 8.58 (1H, dd), 8.92 (1H, d) |
| 160 | 8 | 2-benzofuranyl | | APN: 375; NMR: 7.37-7.59 (2H, m), 8.57 (1H, dd), 8.92 (1H, d) |
| 161 | 8 | 4-BnO—3-NC—Ph— | | APN: 430; NMR: 5.40 (2H, s), 7.99 (1H, dd), 8.91 (1H, d) |
| 162 | 8 | 2,4-diMeO—Ph— | | APN: 359; NMR: 3.85 (3H, s), 7.85 (1H, dd), 8.90 (1H, d) |
| 163 | 8 | 4-MeS—Ph— | | APN: 345; NMR: 2.56 (3H, s), 8.53 (1H, dd), 8.91 (1H, d) |
| 164 | 8 | 4-(CF$_3$)O—Ph— | | APN: 383; NMR: 7.58 (2H, d), 8.57 (1H, dd), 8.92 (1H, d) |
| 165 | 8 | 4-EtO—Ph— | | APN: 343; NMR: 4.12 (2H, q), 7.85 (1H, dd), 8.90 (1H, d) |
| 166 | 8 | 4-PhO—Ph— | | APN: 391; NMR: 7.12-7.18 (4H, m), 7.86 (1H, dd), 8.53 (1H, dd) |
| 167 | 8 | 3,4-diMeO—Ph— | | APN: 359; NMR: 3.85 (6H, d), 7.85 (1H, dd), 8.90 (1H, d) |
| 168 | 8 | 4-Me$_2$N—Ph— | | APN: 342; NMR: 3.00 (6H, s), 7.83 (1H, dd), 8.89 (1H, d) |

TABLE 12-continued

| | | | |
|---|---|---|---|
| 169 | 8 |  | APN: 343; NMR: 6.14 (2H, s), 7.85 (1H, dd), 8.91 (1H, d) |
| 170 | 8 | 3-Ph—Ph— | APN: 375; NMR: 7.35-7.60 (3H, m), 8.57 (1H, dd), 8.91 (1H, d) |
| 171 | 8 | 4-MeO—3-Me—Ph— | APN: 343; NMR: 2.24 (3H, s), 7.85 (1H, dd), 8.90 (1H, d) |
| 172 | 8 | 4-MeO—3,5-diMe—Ph— | APN: 357; NMR: 3.74 (3H, s), 7.85 (1H, dd), 8.90 (1H, d) |
| 173 | 8 | 3-Me-4-(CF₃)O—Ph— | APN: 397; NMR: 2.39 (3H, s), 8.56 (1H, dd), 8.92 (1H, d) |
| 174 | 8 | 4Py— | APN: 300; NMR: 8.51 (1H, s), 8.60 (1H, dd), 8.91 (1H, d) |
| 175 | 8 | 4-MeO—2,5-diMe—Ph— | APN: 357; NMR: 2.16 (6H, s), 7.86 (1H, dd), 8.91 (1H, d) |

TABLE 13

| | | | | |
|---|---|---|---|---|
| 176 | 8 | 4-nBuO—Ph— | | APN: 371; NMR: 0.96 (3H, t), 7.85 (1H, dd), 8.90 (1H, d) |
| 177 | 8 |  | | APN: 341; NMR: 4.63 (2H, t), 7.72 (1H, d), 8.90 (1H, dd) |
| 178 | 9 |  | Na | F: 363 (Na); NMR: 7.25-7.43 (2H, m), 7.94 (1H, d), 8.68 (1H, s) |
| 179 | 9 |  | Na | F: 341; NMR: 7.35 (1H, t), 8.41 (1H, s), 8.69 (1H, d) |
| 180 | 9 |  | | APN: 303; NMR: 7.74 (1H, s), 8.71 (1H, d), 8.88 (1H, d) |
| 181 | 9 |  | | AP: 328; NMR: 7.26 (1H, s), 7.98 (1H, s), 8.60 (1H, d) |
| 182 | 9 |  | | APN: 313; NMR: 7.69 (1H, dd), 8.56 (1H, s), 8.69 (1H, dd) |

TABLE 14

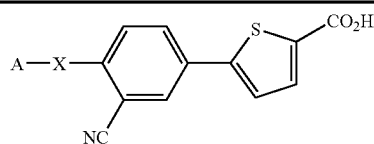

| Ex | Syn | A—X— | Sal | Dat |
|---|---|---|---|---|
| 13 | 13 | 3-H₂N—Ph— | | ES: 321; H: 1.93 |
| 14 | 14 | 4-H₂N—3-F—Ph— | | ES: 339; H: 2.51 |
| 183 | 8 | Ph— | Na | FN: 304; NMR: 7.23 (1H, d), 7.99 (1H, dd), 8.21 (1H, d) |
| 184 | 8 | 4-Me—Ph— | Na | FN: 318; NMR: 2.39 (3H, s), 7.24 (1H, d), 7.35 (2H, d) |
| 185 | 8 | 4-MeO—Ph— | Na | FN: 334; NMR: 3.84 (3H, s), 7.22 (1H, d), 7.95 (1H, dd) |
| 186 | 8 | 4-CF₃—Ph— | Na | F: 374; NMR: 7.25 (1H, d), 8.03 (1H, dd), 8.27 (1H, d) |
| 187 | 8 | 4-Cl—Ph— | Na | FN: 338; NMR: 7.20 (1H, d), 7.58-7.68 (5H, m), 8.22 |

TABLE 14-continued
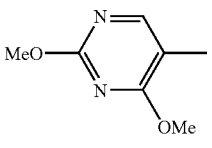
| Ex | Syn | A—X— | Sal | Dat |
|---|---|---|---|---|
| | | | | (1H, d) |
| 188 | 13 | 3Py— | | ES: 307 |
| 189 | 13 | 3-Me—Ph— | | ES: 320 |
| 190 | 13 | 2-Me—Ph— | | ES: 320; H: 2.94 |
| 191 | 13 | 3-HO—Ph— | | ES: 322; H: 2.50 |
| 192 | 13 | 2,3-diMe—Ph— | | ES: 334 |
| 193 | 13 | 3-MeO—Ph— | | ES: 336; H: 2.91 |
TABLE 15
| | | | |
|---|---|---|---|
| 194 | 13 | 2-MeO—Ph— | ES: 336 |
| 195 | 13 | 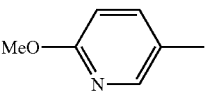 | ES: 337 |
| 196 | 13 | 2-Cl—Ph— | ES: 340; H: 2.90 |
| 197 | 13 | 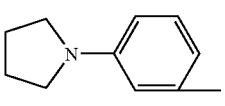 | ES: 345; H: 2.80 |
| 198 | 13 | 4-Ac—Ph— | ES: 348; H: 2.68 |
| 199 | 13 | 4-Me$_2$N—Ph— | ES: 349; H: 2.92 |
| 200 | 13 | 3-Me$_2$N—Ph— | ES: 349; H: 2.49 |
| 201 | 13 | 3-HOOC—Ph— | ES: 350 |
| 202 | 13 | 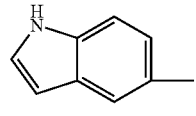 | ES: 354 |
| 203 | 13 | 1Naph- | ES: 356 |
| 204 | 13 | 2Naph- | ES: 356; H: 3.38 |
| 205 | 13 | 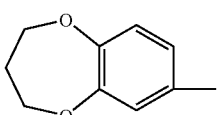 | ES: 357 |
| 206 | 13 | 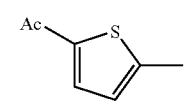 | ES: 359; H: 3.15 |
| 207 | 13 | 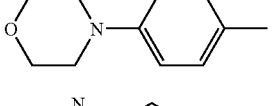 | ES: 362; H: 3.67 |
| 208 | 13 | 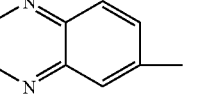 | ES: 362; H: 3.15 |
| 209 | 13 | 4-tBu—Ph— | ES: 362; H: 3.54 |
| 210 | 13 | 3-AcNH—Ph— | ES: 363; H: 2.44 |
| 211 | 13 | 3,4-diMeO—Ph— | ES: 366 |
TABLE 15-continued
| | | | |
|---|---|---|---|
| 212 | 13 | 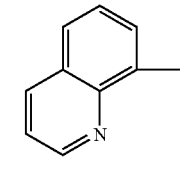 | ES: 368 |
| 213 | 13 | 2-CF$_3$—Ph— | ES: 374; H: 2.92 |
| 214 | 13 | 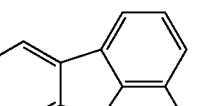 | ES: 375 |
| 215 | 13 | 3-[Me2N(CO)]—Ph— | ES: 377 |
| 216 | 13 | 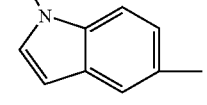 | ES: 378; H: 2.96 |
TABLE 16
| | | | |
|---|---|---|---|
| 217 | 13 | 3-Ph—Ph— | ES: 382; H: 3.46 |
| 218 | 13 | 3-[MeS(O)$_2$]—Ph— | ES: 384 |
| 219 | 13 | 4-cHex-Ph— | ES: 388; H: 3.84 |
| 220 | 13 | 2-(CF$_3$)O—Ph— | ES: 390 |
| 221 | 13 | 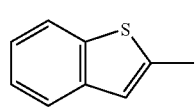 | ES: 391; H: 2.96 |
| 222 | 13 | 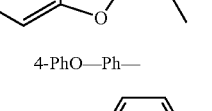 | ES: 358 |
| 223 | 13 | 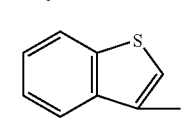 | ES: 396; H: 3.37 |
| 224 | 13 | 4-PhO—Ph— | ES: 398; H: 3.46 |
| 225 | 13 | 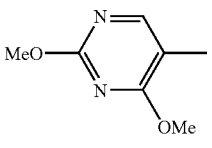 | ES: 412; H: 3.46 |

TABLE 16-continued

| | | | |
|---|---|---|---|
| 226 | 13 | 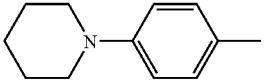 | ES: 389 |
| 227 | 14 | 4-H$_2$N—3-MeO—Ph— | ES: 351; H: 3.19 |
| 228 | 13 | 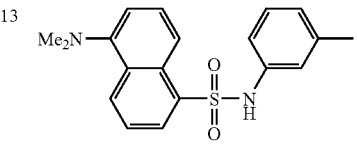 | ES: 554; H: 3.02 |
| 229 | 13 | 4-AcNH—Ph— | ES: 363; H: 2.43 |
| 230 | 13 | 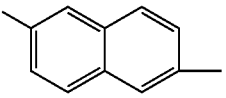 | ES: 386; H: 3.43 |

TABLE 16-continued

| | | | |
|---|---|---|---|
| 231 | 13 | 2-PhO—Ph— | ES: 398 |
| 232 | 13 | 4-[Ph(CO)]—Ph— | ES: 410; H: 3.20 |
| 233 | 13 | 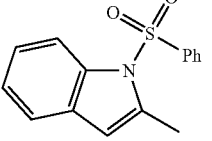 | ES: 485 |
| 234 | 13 | 4-iPrO—Ph— | ES: 364; H: 3.26 |
| 235 | 13 | 4-BnO—Ph— | ES: 412; H: 3.51 |
| 236 | 13 | 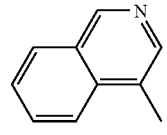 | ES: 357; H: 2.07 |

TABLE 17

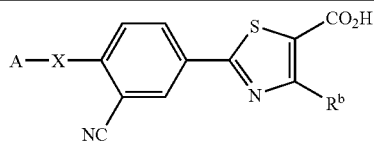

| Ex | Syn | A—X— | R$^b$— | Sal | Dat |
|---|---|---|---|---|---|
| 237 | 8 | Ph— | Me— | | AP: 321; NMR: 2.71 (3H, s), 7.78 (1H, d), 8.49 (1H, d) |
| 238 | 8 | 4-Me—Ph— | Me— | Na | F: 335; NMR: 2.40 (3H, s), 7.37 (2H, d), 8.20 (1H, dd) |
| 239 | 8 | 4-Et—Ph— | Me— | | AP: 349; NMR: 2.65-2.76 (5H, m), 7.41 (2H, d), 8.47 (1H, d) |
| 240 | 8 | 4-(CF$_3$)O—Ph— | Me— | | AP: 405; NMRC: 2.70 (3H, s), 7.58 (2H, d), 8.51 (1H, d) |
| 241 | 8 | 4-MeO—Ph— | Me— | | AP: 351; NMR: 2.70 (3H, s), 3.85 (3H, s), 8.44 (1H, d) |
| 242 | 8 | 3-MeO—Ph— | Me— | | AP: 373 (Na); NMR: 2.71 (3H, s), 3.84 (3H, s), 8.48 (1H, d) |
| 243 | 8 | 3-Me—Ph— | Me— | | AP: 335; NMR: 2.41 (3H, s), 2.70 (3H, s), 8.32 (1H, dd) |
| 244 | 8 | 4-tBu—Ph— | Me— | | APN: 375; NMR: 1.35 (9H, s), 2.71 (3H, s), 7.77 (1H, d) |
| 245 | 8 | 3Fur- | Me— | | APN: 309; NMR: 2.70 (3H, s), 7.10 (1H, dd), 8.29 (1H, dd) |
| 246 | 8 | 3Thie- | Me— | | APN: 325; NMR: 2.70 (3H, s), 7.57 (1H, dd), 7.87 (1H, d) |
| 247 | 8 | 4-Me$_2$N—Ph— | Me— | | APN: 362; NMR: 2.70 (3H, s), 3.00 (6H, s), 7.71 (1H, d) |
| 248 | 8 | Ph— | Et— | | AP: 357 (Na); NMR: 3.14 (2H, q), 7.52-7.70 (5H, m), 7.78 (1H, d) |
| 249 | 8 | 4-Me—Ph— | Et— | | AP: 371 (Na); NMR: 1.29 (3H, t), 2.40 (3H, s), 7.75 (1H, d) |
| 250 | 8 | Ph— | H— | | APN: 305; NMR: 7.52-7.61 (3H, m), 7.81 (1H, d), 8.50 (1H, s) |

TABLE 18

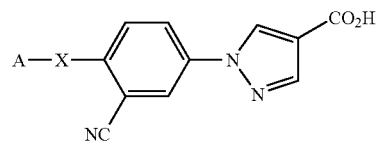

| Ex | Syn | A—X— | Dat |
|---|---|---|---|
| 251 | 8 | Ph— | APN: 288; NMR: 7.46-7.69 (5H, m), 8.55 (1H, d), 9.23 (1H, s) |
| 252 | 8 | 4-Me—Ph— | APN: 302; NMR: 2.40 (3H, s), 8.52 (1H, d), 9.22 (1H, s) |

TABLE 18-continued

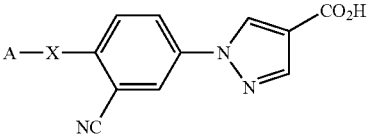

| Ex | Syn | A—X— | Dat |
|---|---|---|---|
| 253 | 8 | 2Thie- | APN: 294; NMR: 7.28 (1H, dd), 7.90 (1H, d), 8.16 (1H, s) |
| 254 | 8 | 4-MeO—Ph— | APN: 318; NMR: 3.84 (3H, s), 7.75 (1H, d), 8.51 (1H, d) |
| 255 | 8 | 3-Me—Ph— | APN: 302; NMR: 2.41 (3H, s), 7.77 (1H, d), 8.17 (1H, s) |
| 256 | 8 | 4-tBu—Ph— | APN: 344; NMR: 1.35 (9H, s), 7.58 (4H, s), 8.16 (1H, s) |
| 257 | 8 | 3Fur- | APN: 278; NMR: 7.08 (1H, dd), 7.90 (1H, d), 9.21 (1H, s) |
| 258 | 8 | 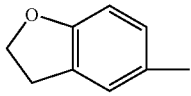 | APN: 330; NMR: 4.62 (2H, t), 7.72 (1H, d), 8.19 (1H, s) |
| 259 | 8 | 3Thie- | APN:294; NMR: 7.55 (1H, dd), 7.88 (1H, d), 9.22 (1H, s) |

TABLE 19

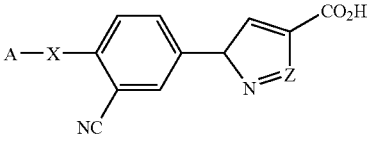

| Ex | Syn | A—X— | Z | Dat |
|---|---|---|---|---|
| 260 | 8 | Ph— | NMe | AP: 326 (Na); NMR: 4.16 (3H, s), 8.25 (1H, dd), 8.39 (1H, d) |
| 261 | 8 | Ph— | O | APN: 289; NMR: 7.81 (1H, d), 7.97 (1H, s), 8.57 (1H, d) |
| 262 | 8 | 4-Me—Ph— | O | APN: 303; NMR: 2.40 (3H, s), 7.78 (1H, d), 7.91 (1H, s) |
| 263 | 8 | 4-tBu—Ph— | O | APN: 345; NMR: 1.35 (9H, s), 7.80 (1H, d), 7.97 (1H, s) |
| 264 | 8 | 3Thie- | O | APN: 295; NMR: 7.67 (1H, dd), 7.98 (1H, d), 8.03 (1H, s) |
| 265 | 8 | 3Fur- | O | APN: 279; NMR: 7.91 (2H, s), 7.93 (1H, s), 8.50 (1H, d) |

TABLE 20

| Ex | Syn | Str | Dat |
|---|---|---|---|
| 266 | 8 | 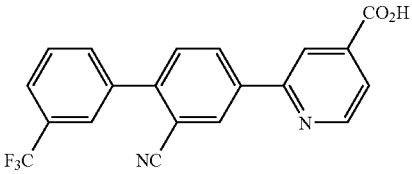 | APN: 367; NMR: 8.03 (1H, s), 8.58 (1H, dd), 8.92 (1H, d) |
| 267 | 8 | 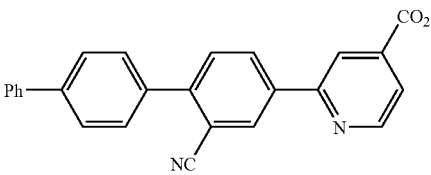 | APN: 375; NMR: 7.37-7.59 (2H, m), 8.57 (1H, dd), 8.92 (1H, d) |
| 268 | 8 | 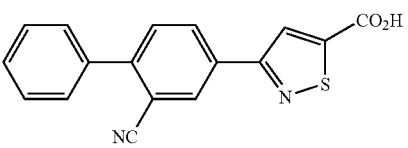 | APN: 305; NMR: 7.78 (1H, d), 8.63 (1H, s), 8.68 (1H, d) |

TABLE 20-continued

| Ex | Syn | Str | Dat |
|---|---|---|---|
| 269 | 8 | tBu—⟨phenyl⟩—⟨phenyl(NC)⟩—⟨isoxazole-S⟩—CO$_2$H | APN: 361; NMR: 1.35 (9H, s), 7.77 (1H, d), 8.62 (1H, s) |

Examples

The pharmacological effect of the non-purine xanthine oxidase inhibitor of the present invention is described with reference to the following Examples. The test results of the compounds of formula (I) for their xanthine oxidase-inhibiting effect are shown as Reference Examples.

Reference Example

Xanthine Oxidase Inhibiting Activity (1) Preparation of Test Compound:
A test compound was dissolved in DMSO (by Nacalai) to have a concentration of 10 mM, and then just before use, its concentration was adjusted to a desired one.
(2) Measurement Method:
The xanthine oxidase inhibitory activity of the compound of the present invention was evaluated according to a partly modified method of a method described in a reference "Free Radic. Biol. Med. 6, 607-615, 1992". Concretely, xanthine oxidase (derived from butter milk, by Sigma) was mixed with 50 mM phosphate buffer to be 0.03 units/ml, and applied to a 96-well plate in an amount of 50 μl/well. The test compound diluted to have a final concentration was added to the plate in an amount of 2 μl/well, and processed at room temperature for 20 minutes. Pterin (by Sigma) was added to it to have a final concentration of 5 μM in an amount of 50 μl/well, and reacted at room temperature for 10 minutes. Under a condition of excitation at 345 nm and emission at 390 nm (pterin is oxidized by xanthine oxidase to give isoxanthopterin, and under the condition it emits light), the sample was analyzed using a microplate reader sapphire (by Tacan).

The light emission by isoxanthopterin in the presence or absence of xanthine oxidase was defined as 0% inhibition and 100% inhibition, respectively, and the concentration (IC$_{50}$) of the test compound for 50% inhibition was computed.

The compounds of formula (I) had good xanthine oxidase inhibiting activity. IC$_{50}$ of typical compounds in Preparation Examples are shown in the following Table 21.

TABLE 21

| Preparation Example | IC$_{50}$ (nM) | Preparation Example | IC$_{50}$ (nM) | Preparation Example | IC$_{50}$ (nM) | Preparation Example | IC$_{50}$ (nM) |
|---|---|---|---|---|---|---|---|
| 1 | 3.6 | 3 | 5.0 | 4 | 1.2 | 6 | 6.9 |
| 7 | 2.2 | 16 | 2.6 | 20 | 10 | 21 | 4.1 |
| 30 | 6.3 | 37 | 4.2 | 40 | 7.3 | 51 | 4.3 |
| 53 | 2.5 | 55 | 1.3 | 59 | 2.8 | 67 | 3.1 |
| 73 | 1.1 | 77 | 2.2 | 82 | 3.1 | 83 | 3.2 |
| 85 | 4.0 | 86 | 5.8 | 92 | 3.2 | 95 | 4.1 |
| 96 | 2.9 | 106 | 2.8 | 109 | 5.1 | 110 | 13 |
| 111 | 2.5 | 113 | 1.8 | 116 | 2.0 | 117 | 5.9 |
| 118 | 6.3 | 132 | 3.7 | 119 | 1.5 | 209 | 0.5 |

IC$_{50}$ of the compounds of Preparation Examples 8 to 14, 133, 138, 141, 143, 145, 153, 158 to 164, 166, 169, 172, 179, 197, 199, 216, 219, 221, 226, 237, 240, 243, 250, 251 and 252 was at most 20 nM.

Patent Reference 1 says that IC$_{50}$ for xanthine oxidase inhibiting activity of the compound A (Example 77 in Patent Reference 1) referred to in the following Example is 1.8 nM. A reference says that IC$_{50}$ for xanthine oxidase inhibiting activity of the compound B (Example 12 in Patent Reference 7) is 5.8 nM (Bioorganic Medicinal Chemistry Letters, 11, 2001, 879-882, Compound No. 5e).

Compound A: 2-(3-cyano-4-isobutyloxyphenyl)-4-methyl-1, 3-thiazole-5-carboxylic acid.

Compound B: 1-(3-cyano-4-neopentyloxyphenyl)-1H-pyrazole-4-carboxylic acid.

The above tests confirm that the compounds as the active ingredient of the pharmaceutical composition of the present invention has a strong xanthine oxidase inhibiting activity.

The compounds as the active ingredient of the pharmaceutical composition of the present invention were tested and evaluated for the therapeutical effect for gastric ulcer and small intestine ulcer, according to the following test methods.

Example 1

Pharmacological Effect in Gastric Ulcer Model

A test compound was suspended in a 0.5% methyl cellulose (MC) solution to prepare a chemical liquid having a concentration 5 ml/kg; and this was orally administered to SD rats (n=12 in each group). The test compound was controlled to be 10 mg/kg or 30 mg/kg. A control group was separately prepared, in which 5 ml/kg of the 0.5% MC solution was orally administered to the rats. After 1 hour, 40 mg/kg of NSAID, diclofenac (by Sigma) was orally administered to all rats of all groups, as a suspension in 0.5% MC solution (5 ml/kg). In 6 hours after the diclofenac administration, the length of the ulcer formed in the gastric corpus was measured using a stereomicroscope (by Nikon) and a micrometer (by Olympus), and the data of 12 cases were averaged. The antiulceration potency (%) of the test compound was computed according to the following formula:

Antiulceration Potency(%): [1−(mean ulcer length of compound-administered group/mean ulcer length of 0.5% MC-administered group)]×100.

As a result, the compounds as the active ingredient of the pharmaceutical composition of the present invention showed a significant (Student's t-test, p<0.05) inhibitory potency, as compared with the control group. The inhibitory potency of each compound is shown in the parenthesis after the Preparation Example Number.

Preparation Example 8 (72%: 30 mg/kg), 183 (27%: 30 mg/kg), 237 (32%: 10 mg/kg), 251 (43%: 30 mg/kg), 254 (32%: 30 mg/kg), Compound A (36%: 30 mg/kg), Compound B (43%: 30 mg/kg).

On the other hand, in the group administered with 30 mg/kg of allopurinol, no inhibitory potency was confirmed. The above results confirm that the compounds as the active ingredient of the pharmaceutical composition of the present invention have an excellent inhibitory effect for gastric ulcer.

Example 2

Pharmacological Effect in Small Intestine Ulcer Model

A test compound was suspended in a 0.5% methyl cellulose (MC) solution to prepare a chemical liquid having a concentration 5 ml/kg; and this was orally administered to SD rats (n=10 in each group). The test compound was controlled to be 10 mg/kg in every case. A control group was separately prepared, in which 5 ml/kg of the 0.5% MC solution was orally administered to the rats. After 1 hour, 10 mg/kg of NSAID, indomethacin (by Sigma) was orally administered to the rats, as a suspension in 0.5% MC solution (5 ml/kg). In 9 hours after the indomethacin administration, the test compound was again orally administered to every rat in the same amount as previously; and after 24 hours, the area of the ulcer formed in the small intestine was measured using a stereomicroscope (by Nikon) and a micrometer (by Olympus), and the data of 10 cases were averaged. The antiulceration potency (%) of the test compound was computed according to the following formula:

Antiulceration Potency(%): [1−(mean ulcer area of compound-administered group/mean ulcer area of 0.5% MC-administered group)]×100.

As a result, all the compounds showed a significant (Student's t-test, p<0.05) inhibitory potency, as compared with the control group. The inhibitory potency of each compound is shown in the parenthesis after the Preparation Example Number.

Preparation Example 8 (29%), 183 (30%), 237 (59%), 250 (73%), 251 (41%), 254 (46%).

On the other hand, in the group administered with 10 mg/kg of allopurinol, no inhibitory potency was confirmed. A proton pump inhibitor used as an agent for treating gastric ulcer, omeprazole (by Sigma) was ineffective in this test. The above results confirm that the compounds as the active ingredient of the pharmaceutical composition of the present invention have an excellent inhibitory effect for small intestine ulcer.

As in the above, the compounds of the present invention showed a remedial effect both in the gastric ulcer model and the small intestine ulcer model, and no conventional remedies could have the effect.

The test results shown in the above-mentioned Examples confirm that the compounds as the active ingredient of the pharmaceutical composition of the present invention have a strong potency of xanthine oxidase inhibition, and in animal tests, the compounds show an excellent effect of curing digestive ulcer. Accordingly, these compounds are expected as an agent for treating or preventing ulcer that forms in digestive tracts by the attack thereto such as gastric acid, pepsin, stress, Helicobacter pylori bacteria or NSAID. Further, the compounds as the active ingredient of the pharmaceutical composition of the present invention do not have a purine structure and their toxicity is low, and accordingly, they are superior to allopurinol in the efficaciousness as so mentioned in the above.

INDUSTRIAL APPLICABILITY

The pharmaceutical composition of the present invention is useful as an agent for treating or preventing ulcer that forms in digestive tracts by the attack of gastric acid, pepsin, stress, Helicobacter pylori, NSAID, etc. In particular, the pharmaceutical composition of the present invention is effective also for ulcer in small intestine, for which remedies for gastric/duodenal ulcer that inhibit gastric acid secretion such as proton pump inhibitors are ineffective, and is therefore useful as an ulcer-treating agent heretofore unknown in the art. In addition, it is superior to allopurinol in the efficaciousness and the safety.

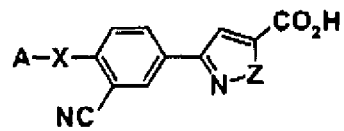

The invention claimed is:

1. A method for treating a stomach or small intestine ulcer, comprising administering an effective amount of at least one non-purine xanthine oxidase inhibitor or a salt thereof to a patient in need thereof, wherein said non-purine xanthine oxidase inhibitor is selected from the group consisting of
    2-(2-cyanobiphenyl-4-yl)isonicotinic acid;
    5-(2-cyanobiphenyl-4-yl)thiophene-2-carboxylic acid;
    2-(2-cyanobiphenyl-4-yl)-4-methyl-1,3-thiazole-5-carboxylic acid;
    2-(2-cyano-4'-methoxybiphenyl-4-yl)-4-methyl-1,3-thiazole-5-carboxylic acid;
    1-(2-cyanobiphenyl-4-yl)-1H-pyrazole-4-carboxylic acid;
    1-(2-cyano-4'-methoxybiphenyl-4-yl)-1H-pyrazole-4-carboxylic acid;
    2-(2-cyanobiphenyl-4-yl)-1,3-thiazole-5-carboxylic acid;
    2-[2-cyano-4'-(trifluoromethoxy)biphenyl-4-yl]-4-methyl-1,3-thiazole-5-carboxylic acid;
    2-(2-cyano-3'-methoxybiphenyl-4-yl)-4-methyl-1,3-thiazole-5-carboxylic acid; and
    2-[2-cyano-4'-(dimethylamino)biphenyl-4-yl]-4-methyl-1,3-thiazole-5-carboxylic acid.

2. A method according to claim 1, which comprises administering 2-(2-cyanobiphenyl-4-yl)isonicotinic acid or a salt thereof.

3. A method according to claim 1, which comprises administering 5-(2-cyanobiphenyl-4-yl)thiophene-2-carboxylic acid or a salt thereof.

4. A method according to claim 1, which comprises administering 2-(2-cyanobiphenyl-4-yl)-4-methyl-1,3-thiazole-5-carboxylic acid or a salt thereof.

5. A method according to claim 1, which comprises administering 2-(2-cyano-4'-methoxybiphenyl-4-yl)-4-methyl-1,3-thiazole-5-carboxylic acid or a salt thereof.

6. A method according to claim 1, which comprises administering 1-(2-cyanobiphenyl-4-yl)-1H-pyrazole-4-carboxylic acid or a salt thereof.

7. A method according to claim 1, which comprises administering 1-(2-cyano-4'-methoxybiphenyl-4-yl)-1H-pyrazole-4-carboxylic acid or a salt thereof.

8. A method according to claim 1, which comprises administering 2-(2-cyanobiphenyl-4-yl)-1,3-thiazole-5-carboxylic acid or a salt thereof.

9. A method according to claim 1, wherein said ulcer is that formed in small intestine.

10. A method according to claim 9, wherein said ulcer is caused by a non-steroidal anti-inflammatory drug.

11. A method according to 1, which comprises administering 2-[2-cyano-4'-(trifluoromethoxy)biphenyl-4-yl]-4-methyl-1,3-thiazole-5-carboxylic acid or a salt thereof.

12. A method according to claim 1, which comprises administering 2-(2-cyano-3'-methoxybiphenyl-4-yl)-4-methyl-1,3-thiazole-5-carboxylic acid or a salt thereof.

13. A method according to claim 1, which comprises administering 2-[2-cyano-4'-(dimethylamino)biphenyl-4-yl]-4-methyl-1,3-thiazole-5-carboxylic acid or a salt thereof.

14. A method according to claim 1, wherein said ulcer is that formed in stomach.

* * * * *

UNITED STATES PATENT AND TRADEMARK OFFICE
CERTIFICATE OF CORRECTION

PATENT NO. : 8,067,446 B2
APPLICATION NO. : 12/280668
DATED : November 29, 2011
INVENTOR(S) : Masakatsu Kawakami et al.

It is certified that error appears in the above-identified patent and that said Letters Patent is hereby corrected as shown below:

The structure (1c) in Col. 14, lines 19-22 should read as follows:

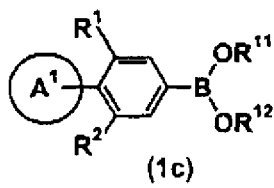

The structure REx 56 in Col. 32, lines 49-52, should read as follows:

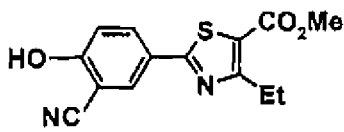

The structure REx 57 in Col. 32, lines 54-58, should read as follows:

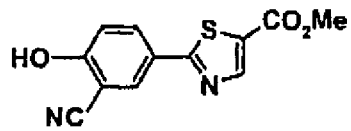

The structure REx 59 in Col. 33, lines 4-8, should read as follows:

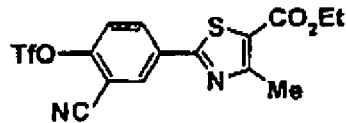

Signed and Sealed this
Tenth Day of April, 2012

David J. Kappos
*Director of the United States Patent and Trademark Office*

CERTIFICATE OF CORRECTION (continued)
U.S. Pat. No. 8,067,446 B2

Page 2 of 2

The structure REx 60 in Col. 33, lines 10-14, should read as follows:

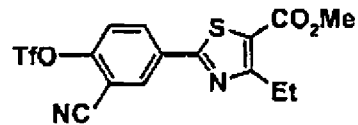

The structure A-X-, Ex. 37 in Col. 35, should read as follows:

PhOCH$_2$CH$_2$O-

The structure in Col. 35, Ex. 49, should read as follows:

PhO-

The structure in Col. 57, Table 19, should read as follows: